US009817481B2

(12) United States Patent
Pantelopoulos et al.

(10) Patent No.: US 9,817,481 B2
(45) Date of Patent: Nov. 14, 2017

(54) METHODS, SYSTEMS, AND APPARATUSES TO DISPLAY VISIBILITY CHANGES RESPONSIVE TO USER GESTURES

(71) Applicant: Fitbit, Inc., San Francisco, CA (US)

(72) Inventors: Alexandros Pantelopoulos, San Francisco, CA (US); Shelten Gee Jao Yuen, Berkeley, CA (US); Heiko Gernot Albert Panther, Oakland, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/876,781

(22) Filed: Oct. 6, 2015

(65) Prior Publication Data

US 2016/0077596 A1    Mar. 17, 2016

Related U.S. Application Data

(63) Continuation of application No. 14/746,748, filed on Jun. 22, 2015.
(Continued)

(51) Int. Cl.
*G06F 3/01* (2006.01)
*G09G 5/10* (2006.01)
(Continued)

(52) U.S. Cl.
CPC ............ *G06F 3/017* (2013.01); *A61B 5/6802* (2013.01); *A61B 5/6824* (2013.01); *G01P 15/00* (2013.01);
(Continued)

(58) Field of Classification Search
CPC . G04B 47/00; A44C 5/00; H04M 1/00; A61B 5/4872; A61B 5/0537; A61B 5/117;
(Continued)

(56) References Cited

U.S. PATENT DOCUMENTS 5,339,294 A    8/1994  Rodgers
5,612,931 A    3/1997  Sato et al.
(Continued)

FOREIGN PATENT DOCUMENTS

EP         1721237 B1        8/2012
WO    WO 2012/170586      12/2012
(Continued)

OTHER PUBLICATIONS

U.S. Office Action, dated Dec. 10, 2015, issued in U.S. Appl. No. 14/876,767.
(Continued)

*Primary Examiner* — Grant Sitta
(74) *Attorney, Agent, or Firm* — Knobbe, Martens, Olson & Bear, LLP

(57)  ABSTRACT

In one embodiment, an electronic device to be worn on a user's forearm includes a display and a set of one or more sensors that provide sensor data. In one aspect, a device may detect, using sensor data obtained from a set of sensors, that a first activity state of a user is active. The device may determine, while the first activity state is active, that the sensor data matches a watch check rule associated with the first activity state. Responsive to the detected match, the device may cause a change in visibility of the display.

20 Claims, 16 Drawing Sheets

Related U.S. Application Data

(60) Provisional application No. 62/068,597, filed on Oct. 24, 2014, provisional application No. 62/054,379, filed on Sep. 23, 2014.

(51) Int. Cl.
  *A61B 5/00* (2006.01)
  *G01P 15/00* (2006.01)

(52) U.S. Cl.
  CPC ......... *G09G 5/10* (2013.01); *G09G 2330/026* (2013.01)

(58) Field of Classification Search
  CPC . A61B 5/0002; A61B 5/02416; A61B 5/0205; A61B 5/1118; A61B 5/681; A61B 5/0022; A61B 5/02438; A61B 5/742; A61B 5/1123; A61B 5/021; A61B 5/02427
  USPC .................................................. 345/156–173
  See application file for complete search history.

(56) References Cited

U.S. PATENT DOCUMENTS

| | | | |
|---|---|---|---|
| 5,946,274 A * | 8/1999 | Yamaguchi | G04C 3/001 307/116 |
| 6,122,959 A | 9/2000 | Hoshal | |
| 6,183,365 B1 | 2/2001 | Tonomura | |
| 6,300,947 B1 | 10/2001 | Kanevsky | |
| 6,397,151 B1 | 5/2002 | Yamagishi | |
| 6,469,718 B1 | 10/2002 | Setogawa et al. | |
| 6,583,369 B2 | 6/2003 | Montagnino et al. | |
| 6,882,955 B1 * | 4/2005 | Ohlenbusch | A43B 3/0005 324/160 |
| 7,254,516 B2 | 8/2007 | Case, Jr. et al. | |
| 7,793,361 B2 | 9/2010 | Ishihara et al. | |
| 7,913,185 B1 | 3/2011 | Benson et al. | |
| 8,180,591 B2 | 5/2012 | Yuen et al. | |
| 8,360,904 B2 * | 1/2013 | Oleson | A63B 24/0062 463/36 |
| 8,365,073 B2 | 1/2013 | Kim et al. | |
| 8,684,900 B2 | 4/2014 | Tran | |
| 8,764,651 B2 | 7/2014 | Tran | |
| 8,784,271 B2 | 7/2014 | Brumback et al. | |
| 8,812,259 B2 | 8/2014 | Messenger et al. | |
| 8,849,697 B2 * | 9/2014 | Tropper | A61B 5/1118 463/36 |
| 8,854,925 B1 * | 10/2014 | Lee | G04G 9/0005 368/10 |
| 8,896,526 B1 | 11/2014 | Park | |
| 9,026,927 B2 | 5/2015 | Brumback et al. | |
| 9,055,164 B2 * | 6/2015 | Hasegawa | G04C 3/002 |
| 9,261,920 B2 | 2/2016 | Wang | |
| 9,274,507 B2 | 3/2016 | Kim | |
| 9,320,457 B2 | 4/2016 | Flaction | |
| 9,600,994 B2 * | 3/2017 | Park | G08B 21/18 |
| 2004/0152957 A1 | 8/2004 | Stivoric et al. | |
| 2005/0245793 A1 | 11/2005 | Hilton et al. | |
| 2006/0028429 A1 * | 2/2006 | Kanevsky | G06F 3/017 345/156 |
| 2006/0090139 A1 | 4/2006 | Jenni et al. | |
| 2006/0242590 A1 | 10/2006 | Polivy et al. | |
| 2007/0049836 A1 | 3/2007 | Chen | |
| 2007/0159926 A1 | 7/2007 | Prstojevich et al. | |
| 2007/0173327 A1 | 7/2007 | Kilgore et al. | |
| 2007/0293371 A1 | 12/2007 | Hilfiker et al. | |
| 2008/0081656 A1 * | 4/2008 | Hiles | G06F 1/1626 455/550.1 |
| 2008/0155455 A1 | 6/2008 | Balasubramanian | |
| 2008/0287751 A1 | 11/2008 | Stivoric et al. | |
| 2009/0164219 A1 * | 6/2009 | Yeung | G04C 3/002 704/258 |
| 2009/0195497 A1 | 8/2009 | Fitzgerald et al. | |
| 2009/0307619 A1 | 12/2009 | Gupta et al. | |
| 2010/0033422 A1 * | 2/2010 | Mucignat | G06F 1/1626 345/156 |
| 2010/0085841 A1 | 4/2010 | Lazaridis et al. | |
| 2010/0117949 A1 | 5/2010 | Lai et al. | |
| 2010/0159995 A1 | 6/2010 | Stallings et al. | |
| 2010/0185064 A1 | 7/2010 | Bandic et al. | |
| 2010/0331145 A1 * | 12/2010 | Lakovic | G04F 10/00 482/8 |
| 2011/0010617 A1 | 1/2011 | Kim et al. | |
| 2011/0025901 A1 * | 2/2011 | Tsubusaki | G06F 1/1694 348/333.12 |
| 2011/0032105 A1 | 2/2011 | Hoffman et al. | |
| 2011/0154196 A1 | 6/2011 | Icho et al. | |
| 2011/0252362 A1 | 10/2011 | Cho et al. | |
| 2012/0036485 A1 * | 2/2012 | Watkins, Jr. | G06F 1/1626 715/863 |
| 2012/0060123 A1 | 3/2012 | Smith | |
| 2012/0083715 A1 | 4/2012 | Yuen et al. | |
| 2012/0084053 A1 | 4/2012 | Yuen et al. | |
| 2012/0274508 A1 * | 11/2012 | Brown | G04F 10/00 342/357.25 |
| 2013/0007665 A1 | 1/2013 | Chaudhri et al. | |
| 2013/0106684 A1 | 5/2013 | Weast et al. | |
| 2013/0119255 A1 * | 5/2013 | Dickinson | G04G 21/00 250/340 |
| 2013/0135203 A1 * | 5/2013 | Croughwell, III | G06F 1/1626 345/158 |
| 2013/0147712 A1 * | 6/2013 | Zhou | G06F 1/1694 345/158 |
| 2013/0190903 A1 | 7/2013 | Balakrishnan et al. | |
| 2013/0197681 A1 | 8/2013 | Alberth, Jr. et al. | |
| 2013/0234924 A1 * | 9/2013 | Janefalkar | G06F 1/1694 345/156 |
| 2013/0254525 A1 | 9/2013 | Johnson et al. | |
| 2013/0274904 A1 * | 10/2013 | Coza | G06F 3/011 700/91 |
| 2013/0290879 A1 | 10/2013 | Greisson | |
| 2013/0324368 A1 | 12/2013 | Aragones et al. | |
| 2014/0099614 A1 * | 4/2014 | Hu | G09B 19/00 434/236 |
| 2014/0139637 A1 * | 5/2014 | Mistry | H04N 5/2252 348/46 |
| 2014/0172362 A1 | 6/2014 | Burton et al. | |
| 2014/0176335 A1 | 6/2014 | Brumback et al. | |
| 2014/0176346 A1 | 6/2014 | Brumback et al. | |
| 2014/0176422 A1 | 6/2014 | Brumback et al. | |
| 2014/0176475 A1 | 6/2014 | Myers et al. | |
| 2014/0180022 A1 | 6/2014 | Stivoric et al. | |
| 2014/0180595 A1 | 6/2014 | Brumback et al. | |
| 2014/0180621 A1 | 6/2014 | Poduri et al. | |
| 2014/0244505 A1 * | 8/2014 | Kim | G06F 3/014 705/44 |
| 2014/0316305 A1 * | 10/2014 | Venkatraman | A61B 5/1112 600/595 |
| 2015/0022438 A1 | 1/2015 | Hong | |
| 2015/0026647 A1 | 1/2015 | Park et al. | |
| 2015/0106052 A1 | 4/2015 | Balakrishnan et al. | |
| 2015/0164377 A1 | 6/2015 | Nathan | |
| 2015/0195679 A1 | 7/2015 | Miyasaka | |
| 2016/0011653 A1 * | 1/2016 | Kotkajuuri | G06F 3/014 713/323 |
| 2016/0018900 A1 * | 1/2016 | Tu | G06F 1/3234 345/156 |
| 2016/0034817 A1 * | 2/2016 | Ali | G06N 5/04 706/46 |

FOREIGN PATENT DOCUMENTS

| | | |
|---|---|---|
| WO | WO 2012/170924 | 12/2012 |
| WO | WO 2012/171032 | 12/2012 |
| WO | WO 2015/127067 | 8/2015 |
| WO | WO 2016/003269 | 1/2016 |

OTHER PUBLICATIONS

"Activator is One of the Best Cydia iPhone Hacks, Control your iPhone with Gestures," Iphone-tips-and-advice.com, [retrieved on

(56) References Cited

OTHER PUBLICATIONS

Jul. 9, 2013 at http://www.iphone-tips-and-advice.com/activatior. html], 10 pp.
"Garmin Swim watch In-Depth Review," Rainmaker, (Jun. 25, 2012, updated Feb. 16, 2013) [retrieved on Sep. 9, 2013 at http://www.dcrainmakercom/2012/06/garmin-swim-in-depth-review. html, 38 pp.
"GPS-Enabled Sport Watch With Wireless Sync," Forerunner® 405 Owner's Manual, (Mar. 2011) Garmin Ltd., 56 pp.
"GPS-Enabled Sport Watch With Wireless Sync," Forerunner® 410 Owner's Manual, (Jul. 2012) Garmin Ltd., 52 pp.
"GPS-Enabled Sport Watch," Forerunner® 110 Owner's Manual, (2010) Garmin Ltd., 16 pp.
"GPS-Enabled Sport Watch," Forerunner® 210 Owner's Manual, (2010) Garmin Ltd., 28 pp.
"GPS-Enabled Sports Watch With Wireless Sync," Forerunner® 405CX Owner's Manual, (Mar. 2009), Garmin Ltd., 56 pp.
"Multisport GPS Training Device," Forerunner® 310XT Owner's Manual, (2009-2013 ), Garmin Ltd., 56 pp.
"Parts of Your Band," (Product Release Date Unknown, downloaded Jul. 22, 2013) Jawbone UP Band, 1 page.
"Samsung Galaxy Gear, Mobile Device, User Manual," 2013, 86 pages, Samsung Telecommunications America, LLC.
"What's in the box," Lark/Larkpro, User Manual, (2012) Lark Technologies, 7 pp.
Alan Chudnow, "Basis Wristband Make Its Debut," (Dec. 3, 2012) The Wired Self, Living in a Wired World, published in Health [retrieved on Jul. 22, 2013 at http://thewiredself.com/health/basis-wrist-band-make-its-debut/], 3pp.
Ambient Sensor and Backlight Auto, Mar. 2013, 6 pages, downloaded from http://forums.getpebble.com/discussion/2891/ambient-sensor-and-backlight-auto on Jun. 22, 2015.
Christina Desmarais, "Which New Activity Tracker is Best for You?" (posted on Sep. 3, 2013) Health and Home, Health & Fitness, Guides & Reviews, [Retrieved on Sep. 23, 2013 at http://www.techlicious.com/guide/which-new-activity-tracker-is-right-for-you/] 4 pp.
Fitbit User's Manual, Last Updated Oct. 22, 2009, 15 pages.
Forerunner® 10 Owner's Manual (Aug. 2012), Garmin Ltd., 10 pp.
Forerunner® 201 personal trainer owner's manual, (Feb. 2006) Garmin Ltd., 48 pp.
Forerunner® 205/305 Owners Manual, GPS-enabled trainer for runners, (2006-2008), Garmin Ltd., 80 pp.
Forerunner® 301 personal trainer owner's manual, (Feb. 2006) Garmin Ltd., 66 pp.
Forerunner® 50 with ANT+Sport™ wireless technology, Owner's Manual, (Nov. 2007) Garmin Ltd., 44 pp.
Forerunner® 910XT Owner's Manual, (Jan. 2013) Garmin Ltd., 56 pp.
Garmin Swim™ Owner's Manual (Jun. 2012), 12 pp.
Jared Newman, "Moto 360 review: Not the Android Wear watch you've been waiting for," Sep. 17, 2014, 10 pages, downloaded from http://www.pcworld.com/article/2684781/moto-360-review-not-the-android-wear-watch-youve-been-waiting-for.html on Oct. 10, 2014.
Larklife, User Manual, (2012) Lark Technologies, 7 pp.
Nike+FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by Tomtom, (Product Release Date Unknown, downloaded Jul. 22, 2013), 42 pages.
Polar WearLink® +Coded Transmitter 31 Coded Transmitter W.I.N.D. User Manual, Polar® Listen to Your Body, Manufactured by Polar Electro Oy, 2010, 11 pages.
RIP EMPSON, "Basis Reveals an Awesome New Affordable Heart and Health Tracker You Can Wear on Your Wrist," (Sep. 22, 2011) [retrieved on Sep. 23, 2013 at http://techcrunch.com/2011/09/22/basis-reveals-an-awesome-new . . . ], 3 pp.
U.S. Final Office Action, dated Jul. 28, 2014, issued in U.S. Appl. No. 14/045,563.
U.S. Final Office Action, dated Jul. 31, 2014, issued in U.S. Appl. No. 14/045,574.
U.S. Notice of Allowability, dated Apr. 8, 2015, issued in U.S. Appl. No. 14/045,574.
U.S. Notice of Allowance, dated Apr. 25, 2014, issued in U.S. Appl. No. 14/045,592.
U.S. Notice of Allowance, dated Jan. 14, 2015, issued in U.S. Appl. No. 14/045,574.
U.S. Office Action, dated Apr. 4, 2014, issued in U.S. Appl. No. 14/045,574.
U.S. Office Action, dated Aug. 10, 2015, issued in U.S. Appl. No. 14/746,748.
U.S. Office Action, dated Feb. 5, 2014, issued in U.S. Appl. No. 14/045,563.
U.S. Office Action, dated Jan. 8, 2014, issued in U.S. Appl. No. 14/045,592.
U.S. Office Action, dated Jul. 17, 2015, issued in U.S. Appl. No. 14/045,563.

* cited by examiner

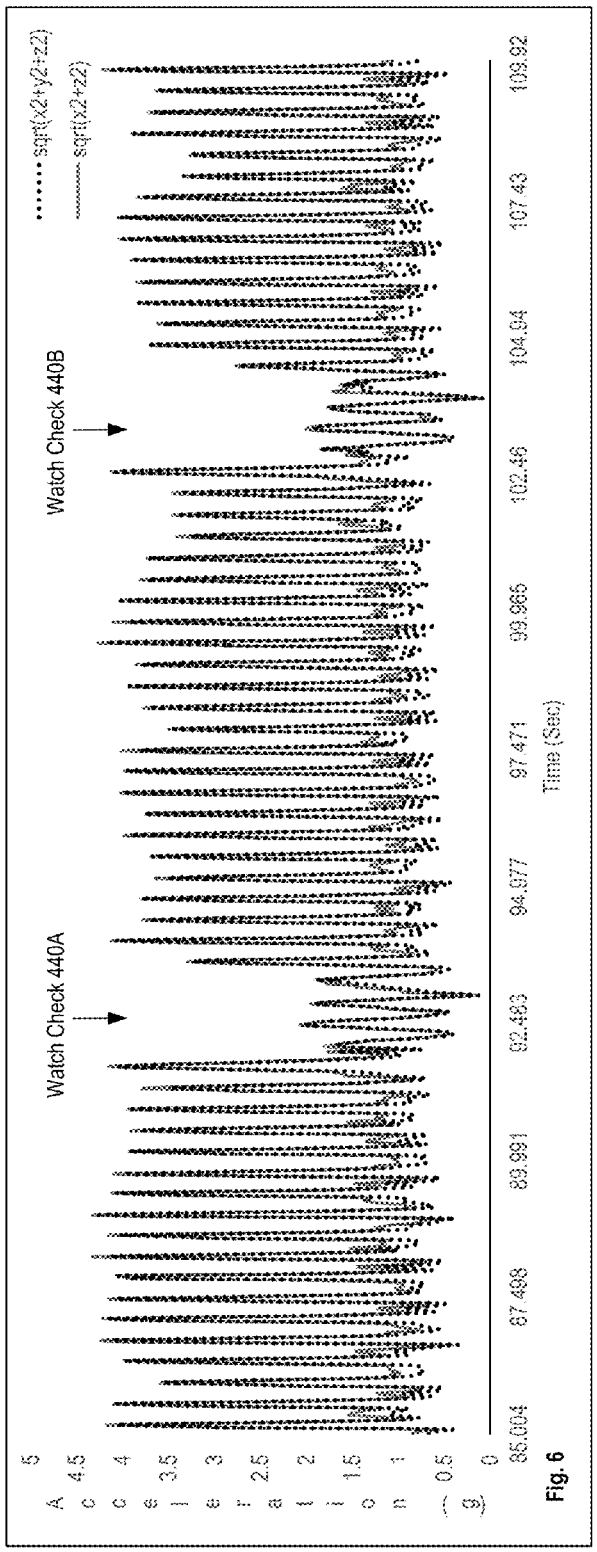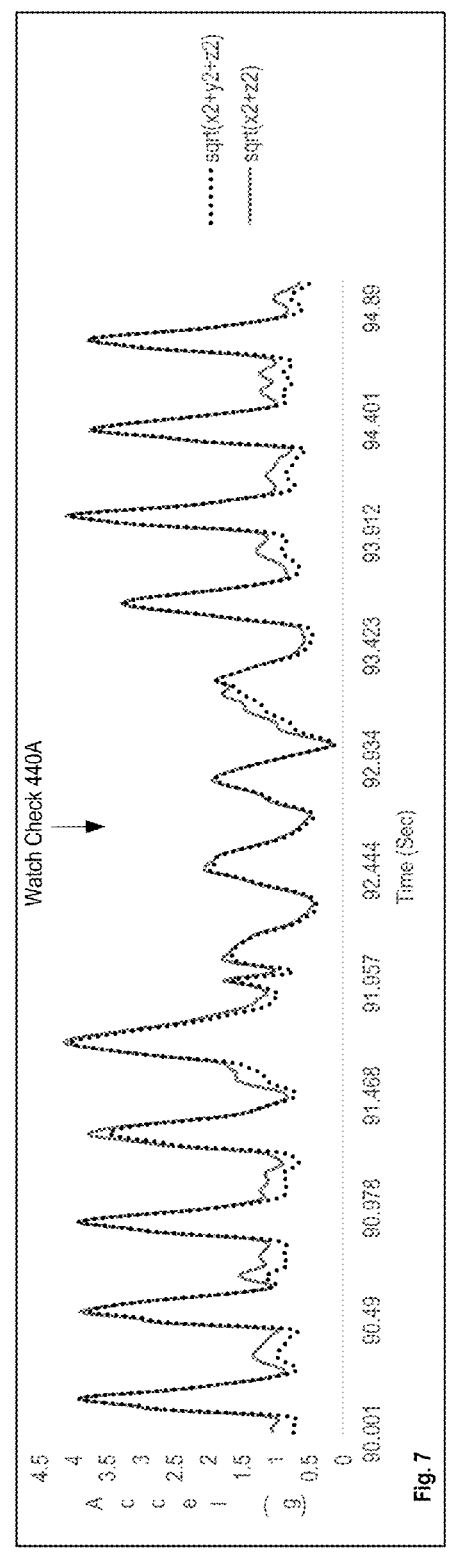
Fig. 6
Fig. 7

METHODS, SYSTEMS, AND APPARATUSES TO DISPLAY VISIBILITY CHANGES RESPONSIVE TO USER GESTURES

CLAIM OF PRIORITY

This application is a continuation of U.S. application Ser. No. 14/746,748, filed Jun. 22, 2015, which claims priority from U.S. Provisional Patent Application No. 62/068,597, filed Oct. 24, 2014, and entitled "Automatic Display Visibility Changes Responsive to User Gestures," and U.S. Provisional Patent Application No. 62/054,379, filed Sep. 23, 2014, and entitled "Automatic Display Visibility Changes Responsive to User Gestures," each of which are herein incorporated by reference.

FIELD

Embodiments relate to the field of electronic devices; and more specifically, to electronic devices to be worn on a user's forearm.

BACKGROUND

Many electronic devices, such as watches, activity trackers, biometric sensor devices, and the like, can be worn on the wrist. For convenience of operation, these wrist worn devices can include displays to interact with the users, such as rendering user interfaces that show, for example, a time, a data, metrics, environmental data, menus, setting, etc. In some cases, the display may only turn on for a limited time based on an explicit user input, such as pressing of a button (virtual or physical), tapping on the display, or the like. Alternatively, the display may always be on so that the user can easily glance at the screen of the device for information.

BRIEF DESCRIPTION OF THE DRAWINGS

The invention may best be understood by referring to the following description and accompanying drawings that are used to illustrate embodiments. In the drawings:

FIG. 6 is a second exemplary line graph illustrating instances when sensor data from a three axis accelerometer is indicative of a user, while running, performing watch check gestures according to one embodiment.

FIG. 7 is an exemplary line graph illustrating a magnification of one of the instances from FIG. 6 according to one embodiment.

DESCRIPTION OF EMBODIMENTS

The following description describes methods and apparatus for automatic display visibility changes responsive to user gestures.

In one example, an apparatus may comprise a display, a set of sensors to generate sensor data, a set of processors coupled to the display and the set of sensors, and a non-transitory machine readable storage medium coupled to the processor. The non-transitory machine readable storage medium may have stored therein instructions, which when executed by the set of processors, cause the set of processors to detect, using the sensor data, that a first activity state of a user is active. Further, the instructions may cause the set of processors to determine, while the first activity state is active, that the sensor data matches a watch check rule associated with the first activity state. Still further, the instructions may cause the set of processor to, responsive to the detected match, cause a change in visibility of the display.

In another example, an embodiment may detect, using sensor data obtained from a set of sensors, that a first activity state of a user is active. The apparatus may determine, while the first activity state is active, that the sensor data represents a set of adjustments that the user would make to view a display of a wristwatch worn on the user's forearm. Responsive to the determination, the embodiment may cause a change in visibility of the display.

Figure 1:
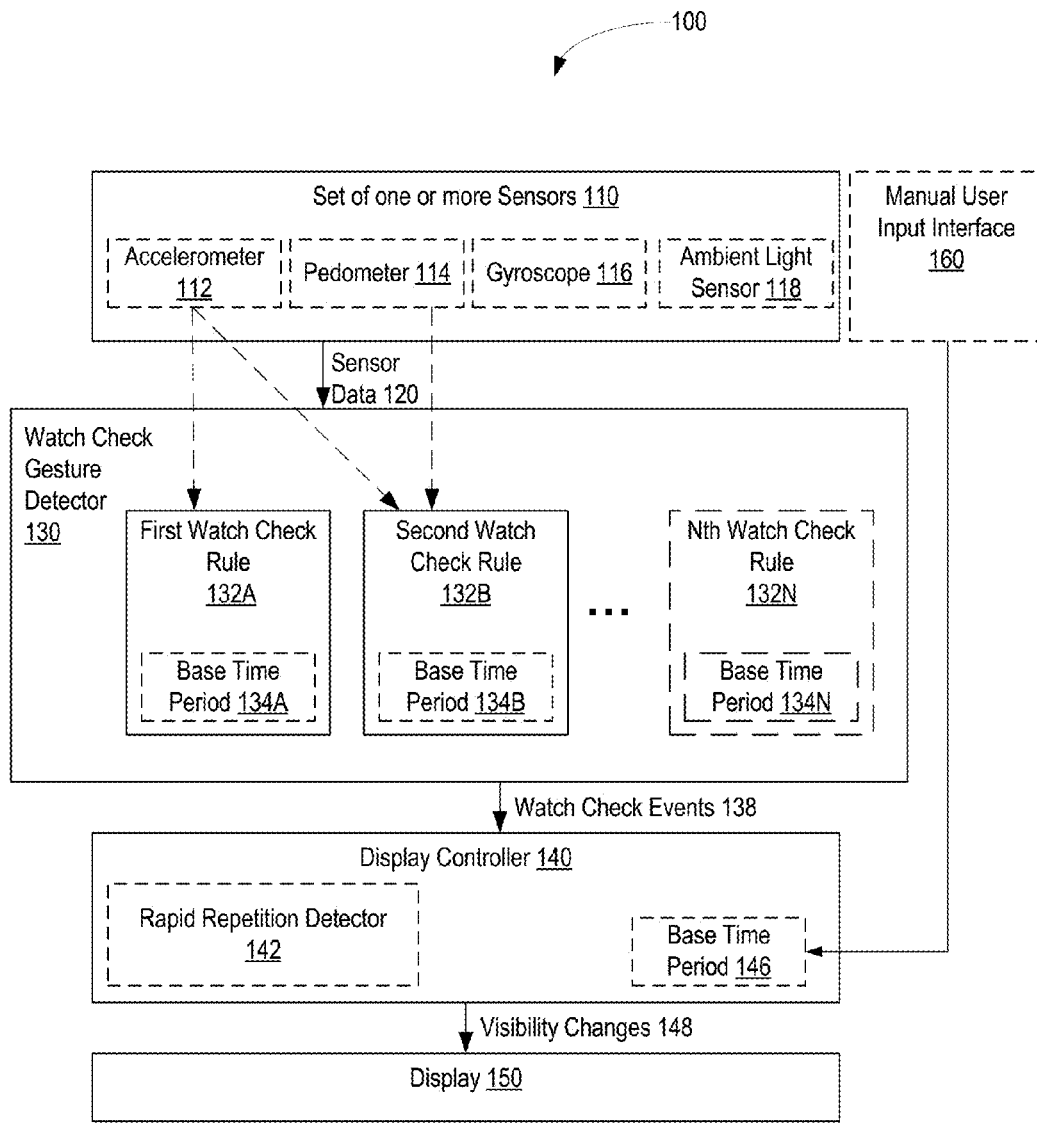
FIG. 1 is a block diagram that illustrates an electronic device that causes display visibility changes responsive to a user performing watch check gestures, according to one embodiment.

FIG. 1 is a block diagram that illustrates an electronic device that causes display visibility changes responsive to a user performing watch check gestures, according to one embodiment. The electronic device 100 in FIG. 1 can be worn on a user's forearm, similar to a band or a watch. Different embodiments allow the device to be worn on the user's forearm in different ways (e.g., wrist-mounted using a wrist-band as illustrated later herein, embedded in a shirt sleeve, etc.).

Some embodiments discussed in the foregoing will be described with reference to a display of the electronic device being generally located on the user's forearm in the same place the display of a wrist watch would be located, and a "watch check gesture" is the movement of a person's forearm to a position typically assumed when a person is checking their wrist-watch (e.g., the person's forearm on which the electronic device is worn moving from a position generally aligned with the sagittal and frontal planes of the person to a position generally aligned with the frontal and transverse planes of the person, in other words the person has moved their forearm from a position generally parallel to the long axis of their body to a position that crosses over their torso in a left-to-right (or right-to-left) direction). While some examples will be described with reference to a display of the electronic device being generally located on the user's forearm in the same place that the display of a wrist watch would be located, example embodiments contemplated by this disclosure are not so limited because modifications to accommodate the electronic device being worn on a different location on the forearm (e.g., higher on the forearm and/or on the opposite side of the forearm) will be apparent to one of ordinary skill in the art.

FIG. 1 illustrates that the device 100 may include a set of one or more sensors 110, which optionally include one or more motion sensors (e.g., an accelerometer 112, a pedometer 114, a gyroscope 116) and an ambient light sensor 118. Sensor data 120 is provided by the set of one or more sensors 110 to a watch check gesture detector 130. By way of example and not limitation, as shown in FIG. 1, the accelerometer 112 may provide sensor data to the watch check gesture detector 130, which may be, in some cases, in the form of samples of acceleration measurements along three axes, labeled x, y, and z. With reference to a 3 axis accelerometer oriented in the electronic device in a particular way (referring to the display of the electronic device, worn on the user's forearm in the same place the display of a wrist watch would be worn, relative to a clock face: the x axis is along the line formed between 12 and 6 o'clock (the positive direction being the 12 to 6 direction) and may also be referred to as the top-bottom axis of the display; the y axis is along a line formed between 9 and 3 o'clock (that is, from the user's elbow to wrist if worn on the left hand) (the positive direction being the 9 to 3 direction) and may also be referred to as the left-right axis of the display; the z axis is along a line perpendicular to the clock face (the positive direction being out the front of the clock face) and may also be referred to as the back-front axis of the display; and thus the x-y axes form a plane that contains the display/clock face and the x-z axes form a plane that is perpendicular to the user's forearm), alternative embodiments may have a different orientation (which will require predictable changes in the techniques described herein).

The watch check gesture detector 130 includes a set of two or more watch check rules 132 (a first watch check rule 132A, a second watch check rule 132B, and up to an Nth watch check rule 132N). The watch check gesture detector 130 may include instructions stored in computer-readable medium that, when executed, cause one or more processors to operate according to the methods disclosed herein. In other cases, the watch check gesture detector 130 may include specific hardware elements or circuitry for executing the operations discussed herein. Different ones of the watch check rules 132A-N may use sensor data from the same or different ones of the set of sensors 110. While in one embodiment all of the set of watch check rules 132 only use sensor data from one of the set of sensors 110 (e.g., a single three axis accelerometer because such a sensor requires less power relative to some other types of sensors), in alternative embodiments, different ones of the set of watch check rules 132 use sensor data from different ones of the set of sensors 110. For example, FIG. 1 shows that both the first watch check rule 132A and the second watch check rule 132B receive sensor data from the accelerometer 112, but only the second watch check rule 132B receives sensor data from the pedometer 114.

Each of the watch check rules 132 determine instances of watch check events when the sensor data 120 (albeit, it may only look at data from a subset of the sensors as described above) is indicative of the user, while performing a particular type of activity, having made a particular set of one or more adjustments that the user would make to view a display of a wristwatch worn on the user's forearm during the user's performance of the particular type of activity. These instances may be referred to herein as watch check events and are collectively represented in FIG. 1 as watch check events 138 which are provided by the watch check gesture detector 130 to a display controller 140. The display controller 140 may include instructions stored in computer-readable medium that, when executed, cause one or more processors to operate according to the methods disclosed herein. In other cases, the display controller 140 may include specific hardware elements or circuitry for executing the operations discussed herein.

In one embodiment, the determinations of instances by one or more of watch check rules 132 include the detection of signatures in the sensor data (referred to herein as sensor data signatures). Each watch check rule 132A-N may detect a different sensor data signature.

As expressed in examples below, in addition to activities such as "running," the term "activity" may include the user being stationary (e.g., sitting, standing). Each "activity type" or "type of activity" may include a single activity (e.g., running) or a group of activities (e.g., walking, hiking, and stationary (where "stationary" may include sitting or standing)). Thus, different embodiments may group more, less, or different activities within different "activity types." For example, as expressed in more detail below, embodiments may group multiple activities within the activity type of a single watch check rule, but tune (e.g., reduce/increase sensitivity depending on whether the user is walking or stationary, change from measuring for a particular threshold along a given axis to measuring for that threshold on a different axis (e.g., if the user's posture changed from vertical to lying down)) the determination of the watch check rules based on which of those activities the electronic device believes the user is currently performing. Alternative embodiments may separate such activities into separate watch check rules and forgo such tuning within the watch check rule (e.g., one of watch check rules 132 for each of running, walking, stationary in a vertical posture, stationary in a horizontal posture (lying down), etc.).

FIG. 1 also illustrates that different ones of the watch check rules 132A-N may have different base periods of time 134A-N for the automatic display visibility change to be in effect. That is, the amount of time the display visibility change will be in effect, unless dismissed or extended. For instance, wherein the base period of time expires without extension, the effect of the automatic display visibility change may be reversed.

The display controller 140 causes changes in visibility of the display 150 (illustrated as visibility changes 148) to facilitate the user's viewing of the display based on the watch check events 138. In different embodiments, the change in visibility of the display 150 may take different forms (e.g., turning on the display (e.g., in the case of an OLED display), turning on a back light of the display (e.g., in the case of a liquid-crystal display (LCD))).

In some embodiments, the determination of watch check events and the change in visibility of the display is performed relatively quickly and with relatively low power. For instance, certain embodiments rely on sensor data from relatively low power sensor(s) (e.g., a single three axis accelerometer) and analyze that sensor data for indications that the user made particular sets of adjustments that the user would make to view a display of a wristwatch worn on the user's forearm during the user's performance of the particular types of activities. For example, one embodiment may cause the changes in visibility of the display to occur within 5 seconds of the user having made one of the particular sets of adjustments; another embodiment within half a second; and another embodiment within 400 milliseconds.

In some embodiments, the electronic device may reduce sensitivity or impose a restriction on the number of automatic changes in visibility of the display (responsive to watch checks) adaptively based on the number of such watch check instances over a short time window. For example, if a user is using a screwdriver, the wrist reorients rapidly and repeatedly in a way that could trigger watch check events back-to-back. Thus, embodiment of the electronic device may recognize that a repeating watch check rule is triggering back-to-back watch checks, and so reject subsequent watch check candidate events. To this end, FIG. 1 also illustrates that the display controller 140 may optionally include a rapid repetition detector 142, which tracks how many changes in the visibility of the display have been automatically caused within a time interval. The display controller may also base the automatic causation of changes in visibility of the display 150 to facilitate the user's viewing of the display 150 on the output of the rapid repetition detector 142. For instance, embodiments may implement the display controller 140 to: 1) ignore one or more watch events 138 (i.e., not perform one of the automatic changes in the visibility of the display) when the number of watch checks detected exceeds a threshold within a time interval; 2) decrease the sensitivity level of the automatic watch check gesture detector 130 (or individual ones of the rules 132A-N) responsive to the automatic causation of a threshold number of changes in the visibility of the display within a time interval.

In addition, FIG. 1 illustrates a manual user input interface 160 (e.g. a button, a touch interface, a sensor to detect a double-tap) may also be implemented which may be used to manually trigger a change in the visibility of the display 150 to facilitate the user's viewing of the display 150 (e.g., by the user operating the electronic device using the user's hand of the user's arm opposite than that of the user's forearm on which the electronic device is being worn). FIG. 1 also illustrates that such a manual triggering may have a different base time period 146. While one embodiment has been described in which different base time periods are implemented, alternative embodiments may use less base periods of time or the same base of time for all such cases.

Figure 2:
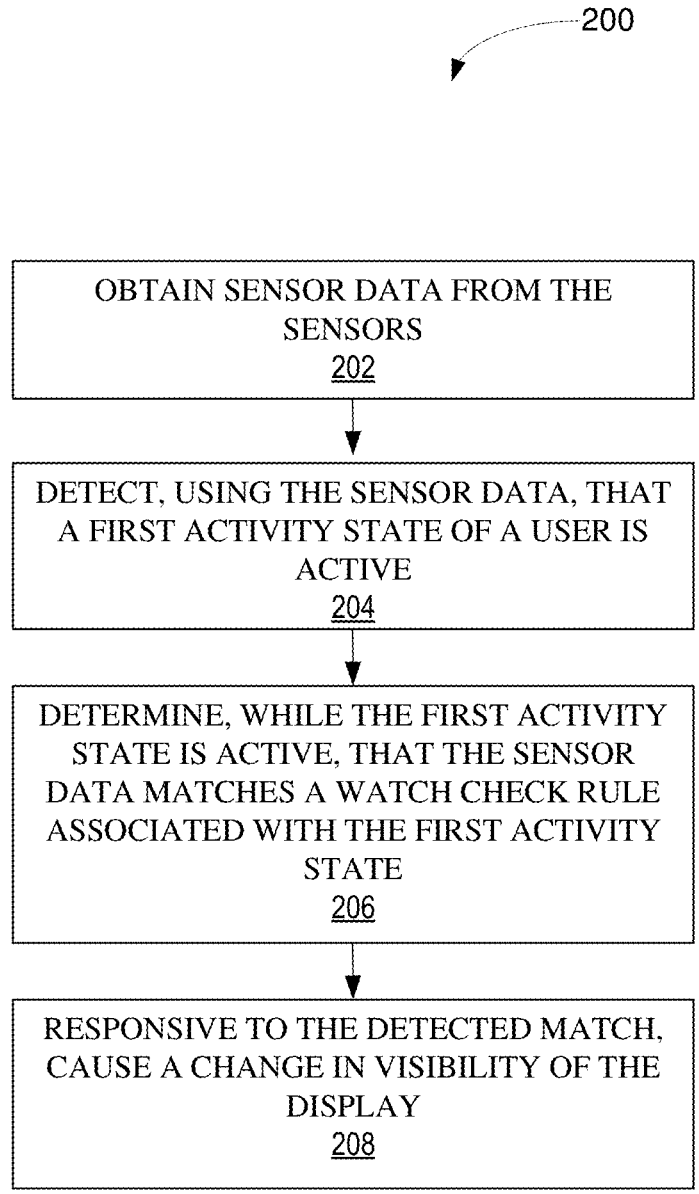
FIG. 2 is a flow diagram illustrating a method for automatic watch check gesture detection based on activity type, according to one embodiment.

FIG. 2 is a flow diagram illustrating a method 200 for automatic watch check gesture detection based on activity type, according to one embodiment. In one embodiment the flow of FIG. 2 is performed by watch check gesture detector according to at least one of the watch check rules 132.

The method 200 may begin at block 202 when the watch check gesture detector obtains sensor data from the sensors. The sensor data may be one or more samples from a three axis accelerometer. Once obtained, the watch check gesture detector may perform one or more transformations on the samples, such as packing the data from a 16-bit value to a lower resolution value (e.g., 10 or less bits), rotating the values from the samples to reflect a difference in orientation of the sensor and the display, or the like. As just described, some embodiments may pack the sensor data into a smaller data size, such as 10 bits or less. Some embodiments may select to pack the sample for an acceleration into an 8-bit word. Such packing may be beneficial in that 8-bits would both reduce memory utilization and bandwidth used to buffer the samples while, at the same time, allow for natively supported memory addressing models of the processor. Operation 202 may also involve the watch check gesture detector down sampling the sensor data obtained from the sensors. For example, the watch check gesture detector may receive sensor data at a frequency of 100 Hz. The watch check gesture may then filter or otherwise smooth that sensor data. The watch check gesture may then buffer or otherwise operate on the filtered data using a rate that is less than the sampling frequency, such as at 25 Hz.

At block 204, the watch check gesture detector may detect, using the sensor data, that a first activity state of a user is active. For example, as is discussed in greater detail below, the watch check gesture detector may determine that the sensor data reflects that the activity being performed by the user is running (e.g., a running activity) based on detecting a determinable number of peaks in acceleration in the sensor data that exceed a given magnitude threshold for a given period of time. Alternatively or additionally, the watch check gesture detector may determine whether the user is performing another type of activity, such as an activity that is associated with the user being relatively stationary or walking. Activities can also be identified as a negative of one type of activity being active, such as a running activity and a non-running activity. While the method 200 is described as determining an activity for the user based on movement patterns represented by the sensor data, other embodiments may determine the activity of the user via other mechanisms. For example, the watch check gesture detector may support different activity modes that are entered automatically based on the sensor data (in similar manner as block 204, but as part of automatic detection for entering activity modes) and/or manually through user input, and the activity mode defines the particular type of activity the user is performing (e.g., which of the watch check rules are currently active) or selectively performs block 204 under only certain conditions (e.g., when the electronic device is not currently in an activity mode).

At block 206, the watch check gesture detector may determine, while the first activity state is active, that the sensor data matches a watch check rule associated with the first activity state. The watch check gesture detector may determine that sensor data matches a watch check rule when the sensor data matches the pattern of movement represented by the watch check rule over for a number of samples. Block 206 illustrates that different watch check rules may be associated with different activities. Thus, while one activity is active, the watch check rules not associated with that activity are disabled and do not cause a watch check event even if the sensor data reflects a pattern of motion specified by that disabled watch check rule.

At block 208, responsive to the detected match, the watch check gesture detector may cause a change in visibility of the display. In some cases, block 208 may involve the watch check gesture detectors signaling the display controller that a watch check event has been detected. In such a case, the display controller may perform a number of operations before changing the visibility of the display, such as, for example, determining that a number of watch check events have not occurred with a determinable time period.

Accordingly, the method 200 may be performed such that different watch check rules may be tailored for specific activities performed by a user. For example, one or more watch check rules may be tailored for use when the watch check gesture detector determines that the sensor data reflects that the user is running. One or more other watch check rules may, on the other hand, be tailored for use when the user is performing other activities, such as sleeping, walking, or being stationary. In some cases, the other watch check rules may be enabled or otherwise activated when the watch check gesture detector determines that the user is not performing an activity, such as not running.

Figure 3:
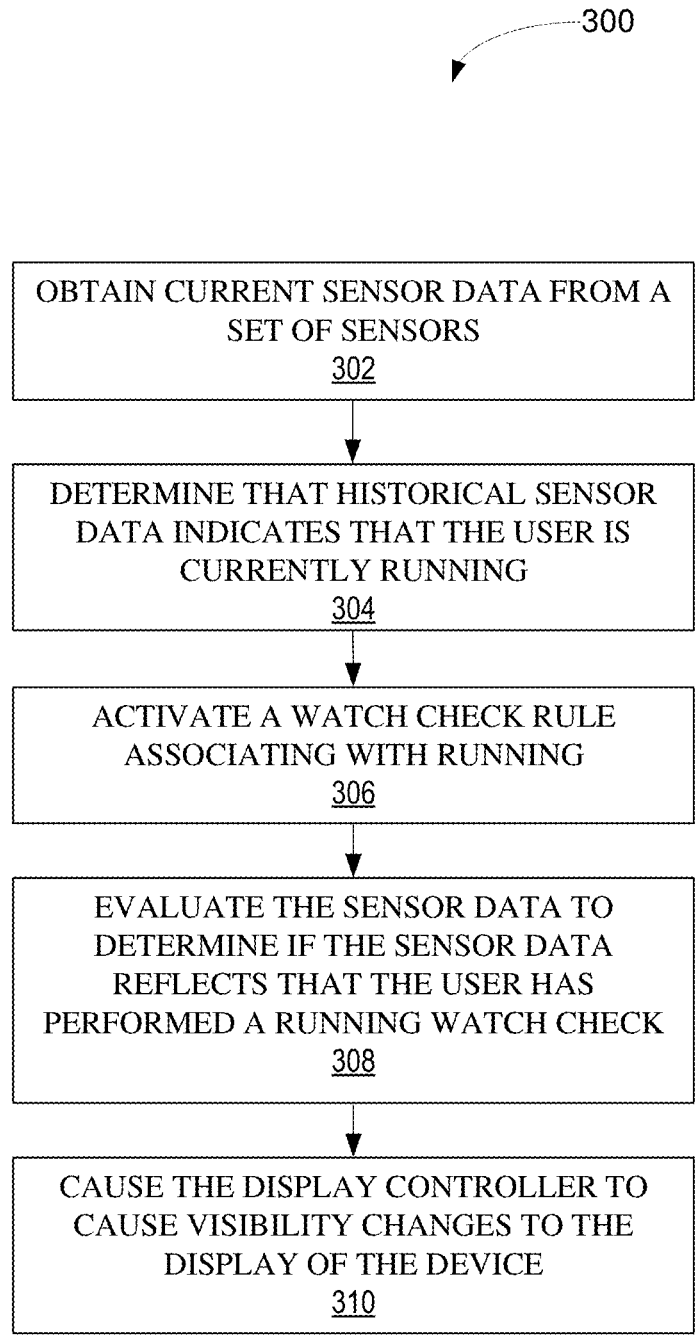
FIG. 3 is a flow diagram illustrating a method for performing automatic watch check gesture detection based on a first exemplary activity type (running), according to one embodiment.

As just described, one type of watch check rule may be activated when the watch check gesture detector determines that the sensor data reflects that the user is running. FIG. 3 is a flow diagram illustrating a method 300 for performing automatic watch check gesture detection based on a first exemplary activity type (running), according to one embodiment.

The method 300 may begin at block 302 when a watch check gesture detector obtains current sensor data from a set of sensors, such as, for example, a 3 axis accelerometer. Alternative or additionally, the sensor data may be obtained from one or more other sensors, such as, for example, a gyroscope, multiple single axis accelerometers, an altimeter, or any other suitable motion detector. Once obtained, the watch check gesture detector may perform one or more transformations on the samples, such as packing the data from a 16-bit value to a lower resolution value (e.g., 10 or less bits), rotating the values from the samples to reflect a difference in orientation of the sensor and the display, or the like.

At block 304, the watch check gesture detector determines that historical sensor data indicates that the user is currently running. The watch check gesture detector can execute block 304 in a number of ways. For example, the watch check gesture detector may track a running feature that is derived from the sensor data (e.g., a 3 axis accelerometer). The watch check gesture detector may calculate the values of the running feature using peaks of acceleration derived from the sensor data. For example, one embodiment of the watch check gesture detector may calculate a square root of the sum of the squares of the acceleration along each of the x, y, and z axes (i.e., sqrt($x^2+y^2+z^2$)). Alternative embodiments may use a different calculation for the values of the running feature. For example, another embodiment of the watch check gesture detector may use the peaks in acceleration of a single axis, such as the x axis. The watch check gesture detector may store the values of the running feature in a data structure such as a circular array, linked list, bounded array, and the like.

To determine whether the historical sensor data indicate that the user is currently running using a running feature that stores values of peaks in acceleration, the watch check gesture detector determines whether a threshold number (e.g., a number that exceeds a quantity threshold) of high magnitude peaks have occurred in the past. The concept of "past," as used herein, can be determined based on a time window or based on the last X values of the running features stored or otherwise captured in the running feature data structure. For example, the running feature data structure may store peaks in acceleration for the last X seconds (e.g., 2.5-10 seconds). Alternatively, the running feature data structure may store the last X peaks in acceleration detected by the watch check gesture detector. To count as a high magnitude peak, the watch check gesture detector may compare the running feature value (e.g., the value of the peak) against a magnitude threshold (e.g., a measurement of g-force, e.g., 1-3 g-forces). If the running feature value exceeds (or, in some cases, equals) the magnitude threshold, then the watch check detector may count that value towards a count of past peaks. Said differently, the watch check gesture detector may filter out running feature values (e.g., peaks in acceleration) that fail to satisfy the magnitude threshold.

In some cases, in performing block 304, the watch check gesture detector may determine whether the last high magnitude peak has occurred close in time to the current sample. For example, the watch check gesture detector may determine whether the last high magnitude is within a specified number of samples or within a specified time period from the current sample.

At block 306, based on determining that the historical sensor data indicates that the user is currently running, the watch check detector may activate a watch check rule associating with running, which may be referred to as a running watch check rule. Activating the running watch check rule may allow the watch check detector to affect the display of the device if the conditions of the running watch check rule are met. In some embodiments, when the watch check detector enables the running watch check rule, the watch check detector may disable the watch check rules for other activities, such as watch check rules for non-running activities.

At block 308, the watch check gesture detector evaluates the sensor data to determine if the sensor data reflects that the user has performed a running watch check. In some cases, in performing block 308, the watch check gesture detector may compare the sensor data against a running watch check rule. The running watch check rule may have one or more conditions. For example, in one case, the watch check gesture detector may determine whether or how many of the most recent acceleration peaks fall below a magnitude threshold. In some embodiments, the magnitude threshold used in block 308 may be the magnitude threshold used to determine whether sensor data reflects that the user is running (see, e.g., description for block 304). In other cases, the magnitude threshold used at block 308 may be different than the magnitude threshold used in block 304. To compute the acceleration magnitude, the watch check gesture detector may, according to one example, compute the square root of the sum of the squares of the acceleration along each of the x, y, and z axes for the current sample. Other examples may use a different calculation that combines the axes or a different approach that compares the different axes individually to thresholds (e.g., peak-to-peak acceleration swings do not exceed 2 g). For example, one example of the watch check gesture detector may calculate the peaks of the acceleration of the x axis which is then compared against the magnitude threshold.

Alternatively or additionally, another condition that a watch check gesture detector may consider is whether the x and y samples are within a reasonable bound for a time period. For example, the watch check gesture detector may evaluate whether the current x or y (or both) value is within a given range of values compared to a sample of x or y (or both) previously received, say 1, 5, 10, 20, 50, or any other suitable number of samples prior to the current sample. Rather than comparing the current value with a past value, the watch check gesture detector may instead compare the max x value with the minimum x value, for a recent time period, to determine whether the value of x has fluctuated much. The same can be done with the values for the y axis. Still further, an embodiment of the watch check gesture detector may determine whether the standard deviation for the x or y values are below a threshold value.

Alternatively or additionally, another condition for a running watch check rule that a watch check gesture detector may consider is whether the acceleration for z is sufficiently large, as may be determined by comparing against a threshold.

Alternatively or additionally, another condition for a running watch check rule that a watch check gesture detector may consider is whether the acceleration for a composite feature is sufficiently large, as may be determined by comparing against a threshold. An example of a composite feature may be:

$$-x+z-abs(y)$$

Where x is the magnitude of acceleration along the x axis, z is the magnitude of acceleration along the z axis, y is the magnitude of acceleration along the y axis, and abs is a function that returns the absolute value for a given input.

At block 310, based on determining that the conditions for the running watch check rule are met, the watch check gesture detector may cause the display controller to cause visibility changes to the display of the device.

Figure 4:
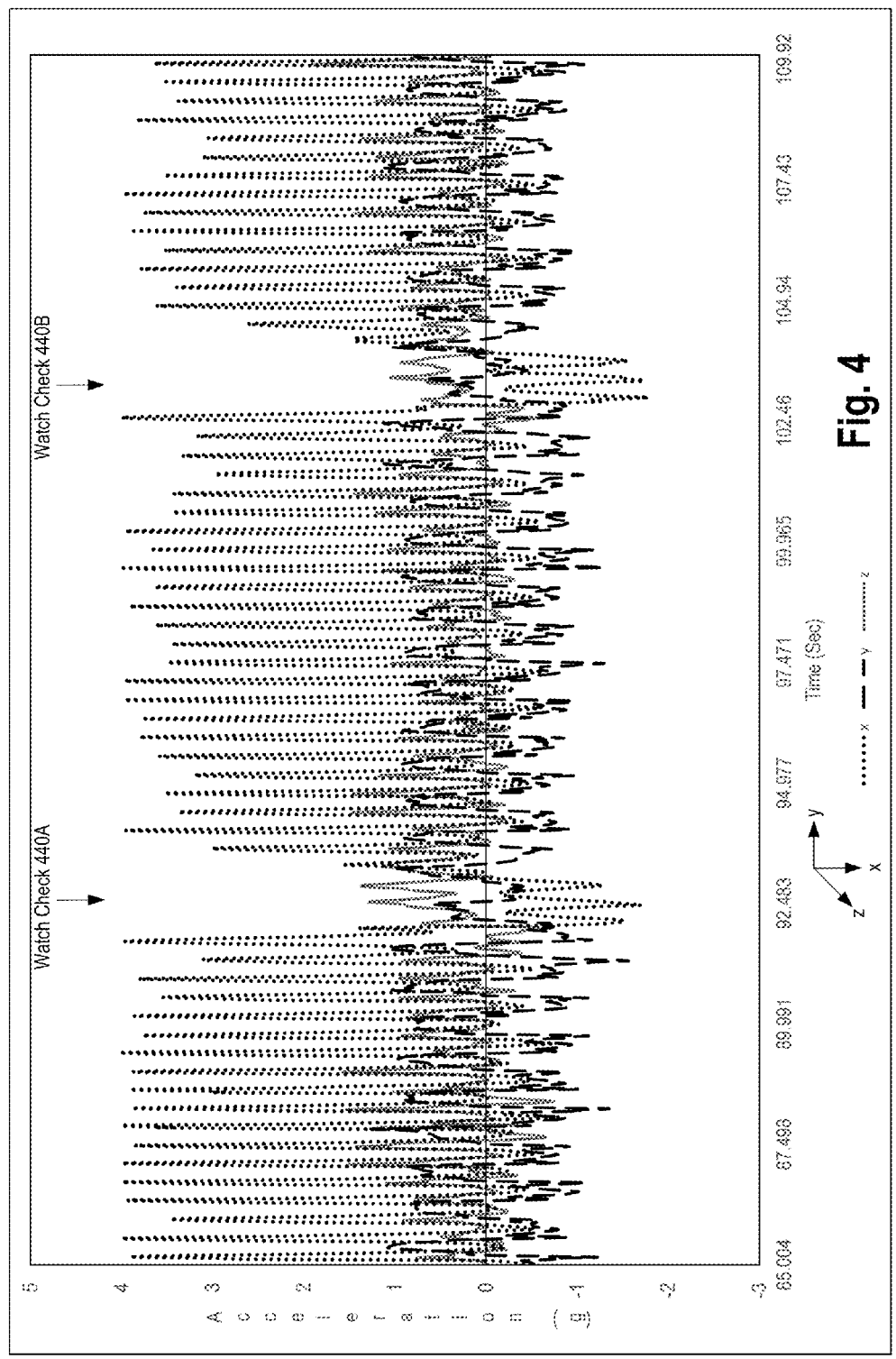
FIG. 4 is an exemplary line graph illustrating when sensor data from a three axis accelerometer is indicative of a user, while running, performing watch check gestures according to one embodiment.

FIG. 4 is an exemplary line graph illustrating when sensor data from a three axis accelerometer is indicative of a user, while running, performing watch check gestures according to one embodiment. FIG. 4 shows the sensor data from the x, y, and z axes of an accelerometer. The graph reflects the relatively large peaks in acceleration along the x, y, and z axes while the user is running, and the changes in acceleration that occur when the user performs watch check gestures 440A and 440B.

Figure 5:
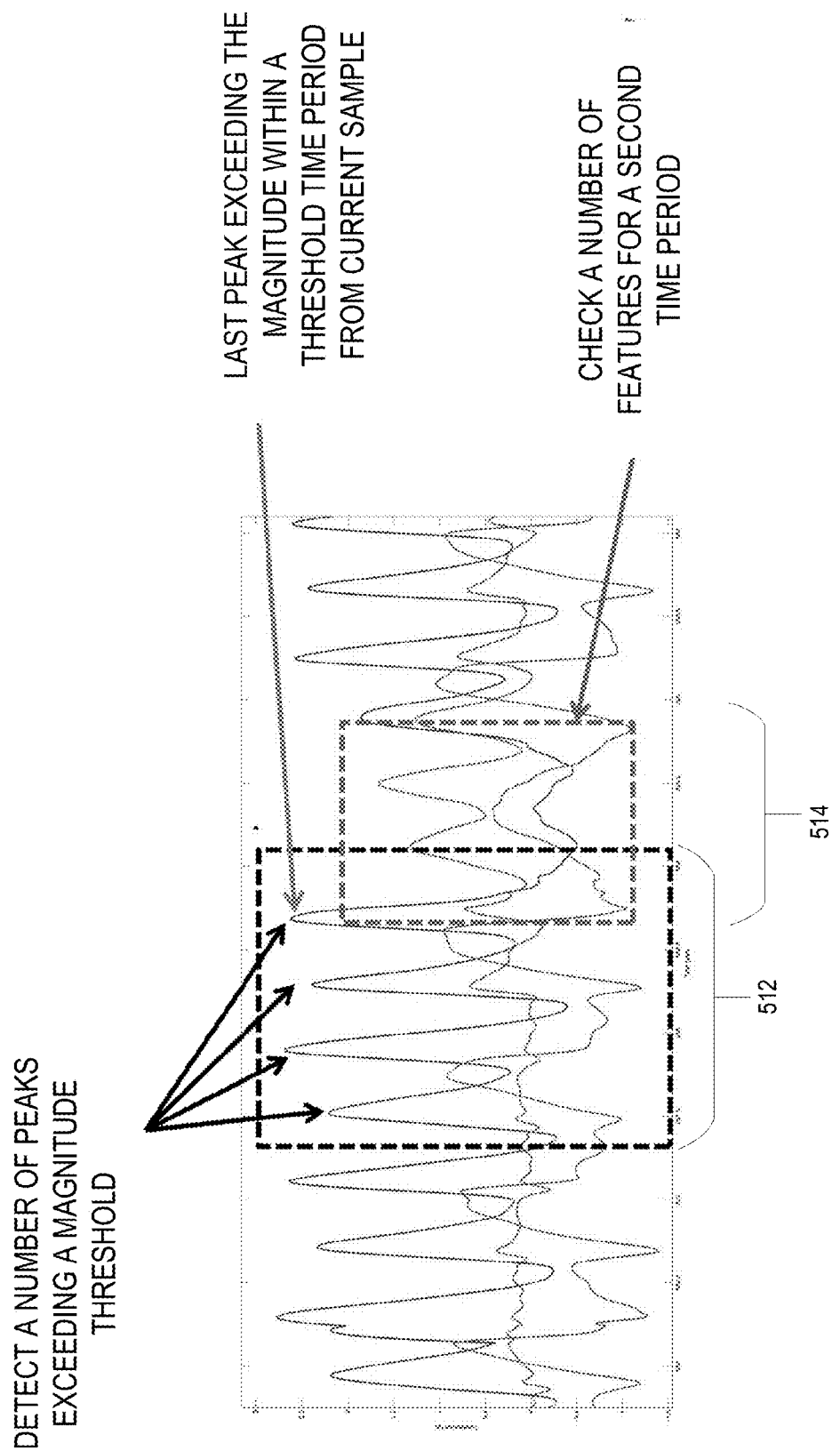
FIG. 5 is an exemplary line graph illustrating a watch check rule that determines when sensor data from a three axis accelerometer is indicative of the user, while running, performing watch check gestures according to one embodiment.

FIG. 5 is an exemplary line graph illustrating a watch check rule that determines when sensor data from a three axis accelerometer is indicative of the user, while running, performing watch check gestures according to one embodiment. For example, the watch check rule shown in FIG. 5 may include a number of conditions. According to one condition, for a time period 512 or set of samples, a number of positive peaks along an x-axis is to exceed a threshold number for the condition to be satisfied or otherwise met. Another condition may specify that the most recent peak that exceeds the magnitude threshold is to be within a time threshold from the most recent current sample. Another condition may specify a number of sub-conditions on the values of the motion data during a second time period 514. One of the sub-conditions may determine whether an increase to a composite value of $-x+z-abs(y)$ for the second time period 514 exceeds a threshold value. Another sub-condition may determine whether the increases to x and y values (or corresponding peaks) are below a threshold value for the second time period 514. Yet another sub-condition may determine whether the increase to the z value (or corresponding peak) is above a threshold value for the second time period.

Although FIG. 5 shows that the first time period 512 and the second time period 514 may overlap, other embodiments may include time periods that do not overlap or are otherwise disjointed.

FIG. 6 is a second exemplary line graph illustrating instances when sensor data from a three axis accelerometer is indicative of a user, while running, performing watch check gestures according to one embodiment. FIG. 6 shows calculations based on the sensor data from the x, y, and z axes of an accelerometer. Specifically, FIG. 6 shows two lines: 1) the calculation of the square root of the sum of the squares of the acceleration along each of the x, y, and z axes; and 2) the calculation of the square root of the sum of the squares of the acceleration along each of the x and z axes. The graph reflects that when the user performs the watch check gesture while running (shown by watch check gestures 440A and 440B of FIG. 4), the current acceleration magnitude along the Y axis is small relative to the current acceleration magnitude along the X and Z axes. More specifically, the lines have a lower degree of separation during the watch checks.

FIG. 7 is an exemplary line graph illustrating a magnification of one of the watch check events from FIG. 6 according to one embodiment.

Figure 8:
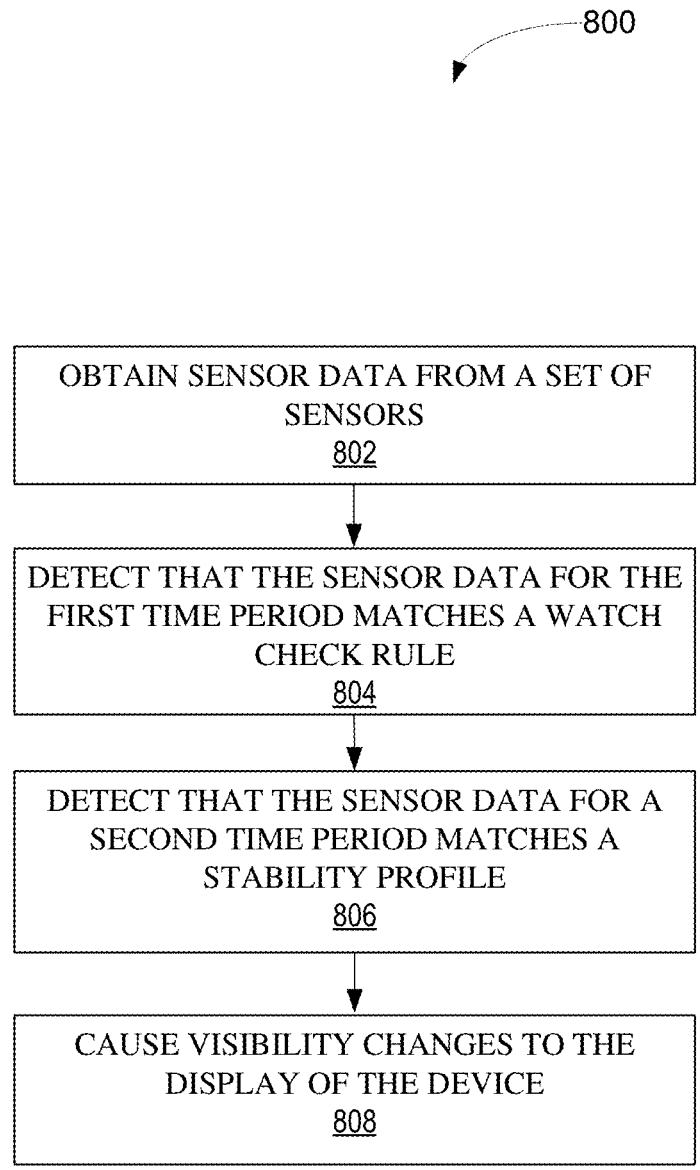
FIG. 8 is a flow diagram illustrating automatic watch check gesture detection based on a second exemplary activity type (non-running—e.g., walking, stationary) according to one embodiment.

FIG. 8 is a flow diagram illustrating automatic watch check gesture detection based on a second exemplary activity type (non-running—e.g., walking, stationary) according to one embodiment.

As FIG. 8 shows, the method 800 begins at block 802 when a watch check gesture detector obtains current sensor data from the sensors, such as a three axis accelerometer, a pedometer, a gyroscope, or any combination thereof. The sensor data obtained at block 802 may be stored in a buffer that stores other sensor data previously obtained by the watch check gesture detector. As is described in greater detail below, the watch check gesture detector may perform one or more operations on the sensor data, such as scaling the sensor data, performing adjustments to the sensor data to account for the orientation of the sensor, and smoothing the sensor data.

At block 804, the watch check gesture detector may detect that the sensor data for the first time period matches a watch check rule. As discussed above, a watch check rule may specify a pattern of movement that may trigger a watch check event. Such patterns of movement may be expressed in terms of acceleration along one or more axes tracked or otherwise measured by an accelerometer, for example. In some cases, the watch check gesture detector may evaluate the sensor data against multiple watch check rules that each express a different pattern of movement that may individually generate a watch check event. Various watch check rules are discussed in greater detail below.

At block 806, the watch check gesture detector may detect that the sensor data for a second time period matches a stability profile. A stability profile may be data or logic that expresses when sensor data reflects that the device is stable. For example, in one example, the watch check gesture detector may use the following formula as a stability profile to determine when the device is stable:

$$(\max(x[n:n+A])-\min(x[n:n+A]))<\text{Range Threshold}$$

Where max( ) is a function that returns the maximum value from a range of values. x[n:n+A] represents a range of acceleration values from nth sample (e.g., the most current sample) to the (n+A)th sample from the x[n] sample going back in time min( ) is a function that returns the minimum value from a range of values. Range Threshold is a threshold value which determines an amount in which the maximum acceleration and minimum acceleration may vary. In some cases, the value Range Threshold may be a constant value. In other cases, the value of Range Threshold may be a dynamic value which may change when, for example, the watch check gesture detector determines that the user is walking.

At block 808, the watch check gesture detector may, responsive to the detected matches, cause a change in visibility of the display. Depending on embodiments, the change performed by the watch check gesture detector may be any combination of illuminating the display, a backlight of the display, changing the content displayed by the display, or the like.

Figure 9:
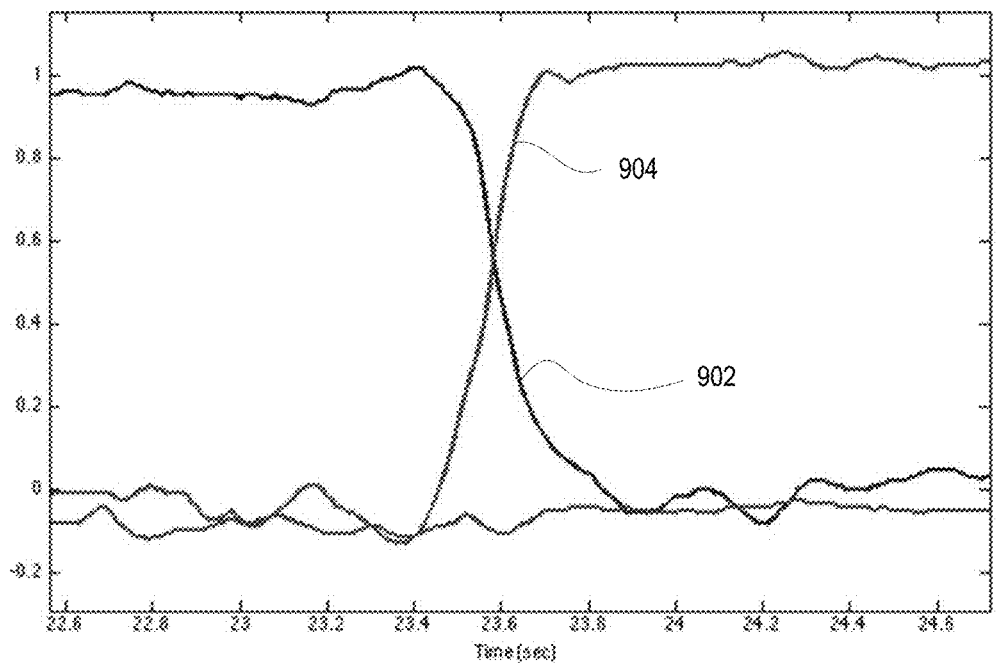
FIGS. 9-12 are diagrams that illustrate patterns of motion which, when detected by the watch check gesture detector, may cause the watch check gesture detector to signal that a watch check event has occurred.

As described above with reference to FIG. 8, embodiments of the watch check gesture detector may analyze the sensor data in light of one or more watch check rules to determine whether the sensor data reflects that a watch check event has occurred. These watch check rules are now discussed in greater detail. For example, FIG. 9 is a diagram that illustrates a pattern of motion which, when detected by the watch check gesture detector, may cause the watch check gesture detector to signal that a watch check event has occurred. The watch check event that corresponds to this type of watch check rule may be referred to herein as a wrist flip watch event. In particular, the watch check rule may specify that the wrist flip watch event occurs when the sensor data indicates that there significant decrease in the accelerometer x-axis (e.g., 902) and, at the same time, a significant increase in the accelerometer z-axis (e.g., 904). Further, the wrist flip watch event may specify that the orientation of the device is facing upwards towards the sky (e.g., normal to the force of Earth's gravitational pull, as may be measured by a force detected on one of the axis of the accelerometer). The physical movement that corresponds to the wrist flip watch event may be where a person wearing the device on their wrist already has their hand somewhat extended (as may be the case where they have their arms on a table top) and simply rotates their arm so that the device facing up and is visible, for example.

Figure 10:
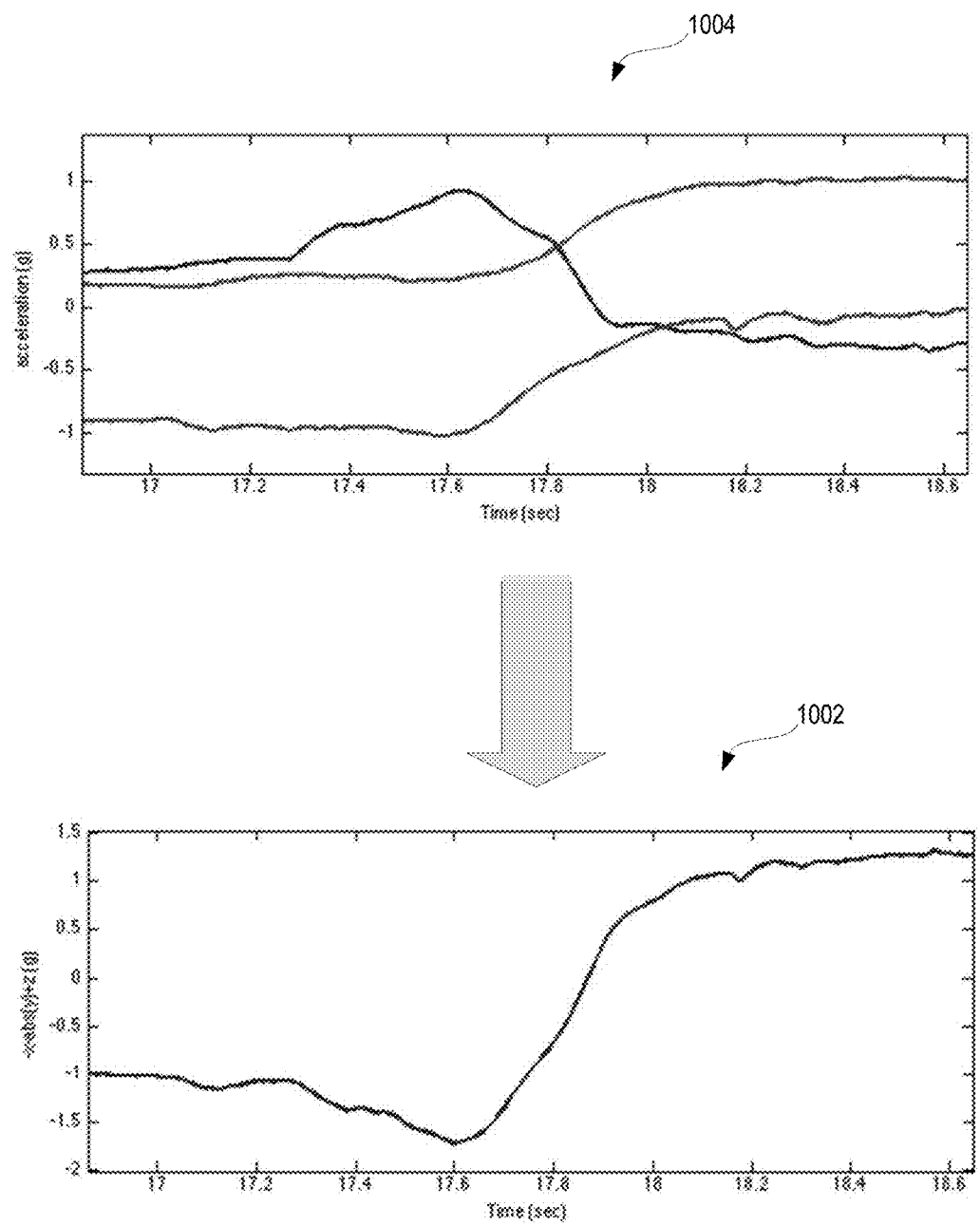

FIG. 10 illustrates another pattern of motion which, when detected by the watch check gesture detector, may cause the watch check gesture detector to signal that a watch check event has occurred. The watch check event that corresponds to this type of watch check rule may be referred to herein as the hand raise watch check event. In particular, the watch check rule may specify that the hand raise watch check event occurs according to a feature defined by a composite value 1002 derived from values from each of the three axes of acceleration 1004 generated by the accelerometer. For example, the feature may be calculated according to the following function:

$$f=-x+abs(y)+z$$

Where f is the value for the composite feature used by the watch check rule that detects hand raise watch check event. The hand raise watch check event may trigger when the watch check gesture detector detects a large increase in the feature f. Further, the hand raise watch check event may specify that the orientation of the device is facing upwards (e.g., as may be measured by the force of gravitational pull on one or more of the axis measured by an accelerometer). The physical movement that corresponds to the hand raise watch check event may be where a person wearing the device on their wrist raises and rotates their arm from a side position to their stomach, with the face of the device facing towards the sky, for example.

Figure 11:
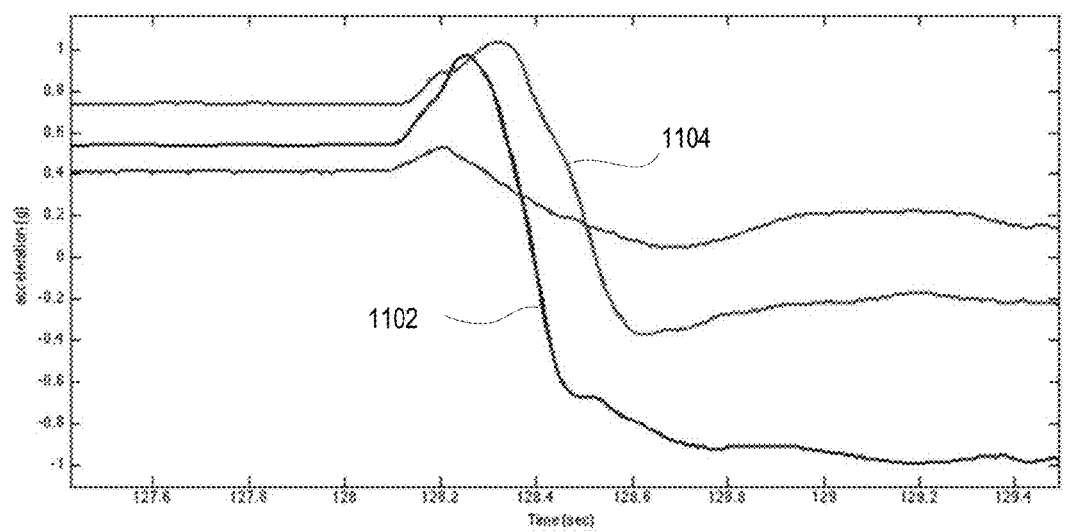

FIG. 11 illustrates another pattern of motion which, when detected by the watch check gesture detector, may cause the watch check gesture detector to signal that a watch check event has occurred. The watch check event that corresponds to this type of watch check rule may be referred to herein as the wrist-to-face watch check event. In particular, the watch check rule may specify that the wrist-to-face watch check event occurs when the sensor data indicates that there is a significant decrease in x-axis 1102, z-axis 1104, or both. Further, the wrist-to-face watch check event may specify that the orientation of the device is facing towards the horizon (e.g., face of the device is normal to the user's face), as may be measured by the force of gravitational pull on one or more of the axis measured by an accelerometer. The physical movement that corresponds to the wrist-to-face watch check event may be where a person wearing the device on their wrist raises their wrist and rotates their arm such that the face of the device is normal to the face of the user, for example.

Figure 12:
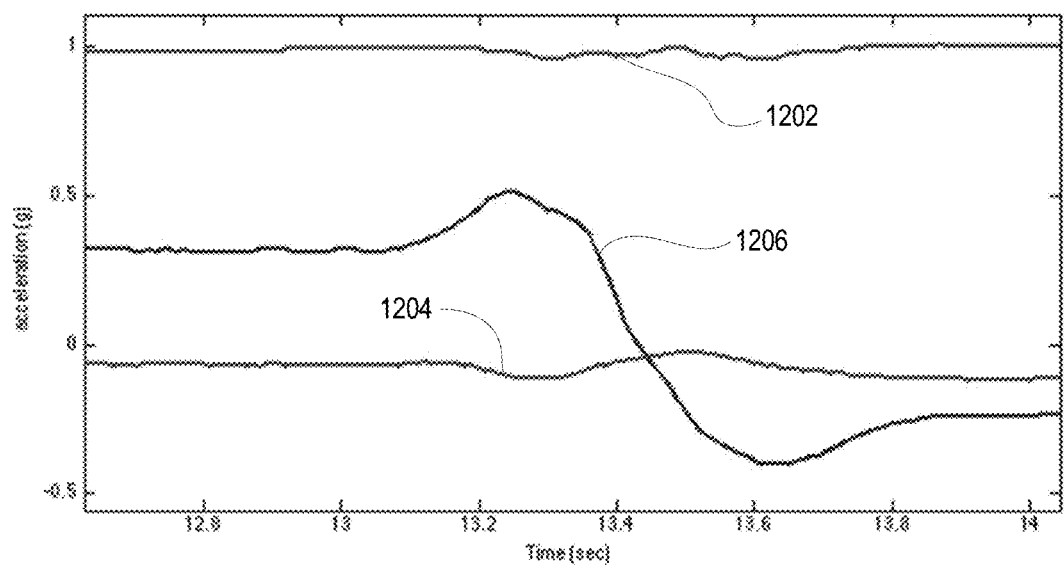

FIG. 12 illustrates another pattern of motion which, when detected by the watch check gesture detector, may cause the watch check gesture detector to signal that a watch check event has occurred. The watch check event that corresponds to this type of watch check rule may be referred to herein as the hand-to-chest watch check event. In particular, the watch check rule may specify that the hand-to-chest watch check event occurs when the sensor data indicates that there is stable values for the accelerations along the z and y axes and a significant decrease in acceleration along the x axis. Further, the hand-to-chest watch check event may specify that the orientation of the device is facing towards the sky (e.g., display face of the device is normal to the force of gravity), as may be measured by the force of gravitational pull on one or more of the axis measured by an accelerometer. The physical movement that corresponds to the hand-to-chest watch check event may be where a person wearing the device on their wrist rotates their forearm from a starting position where the forearm is extended out away from the body of the person (e.g., as if they were typing on a keyboard) to a position where the forearm is across their body, such that the face of the device is facing the sky, for example.

In some cases, the watch check gesture detector may alter the parameters used to detect whether a watch check event has occurred. For example, upon receiving an indication that the user is walking from a pedometer in the device, the watch check gesture detector may vary the parameters such that determining whether the device is stable allows for more motion along one or more axes tracked by the accelerometer. Further, as is described herein, the number of true events detected in the time period may be relaxed. For example the true events threshold may be lowered for instances that the watch check gesture detector detects that the user is walking, as compared to the true event threshold used when the user is determined to be stationary.

Figure 13:
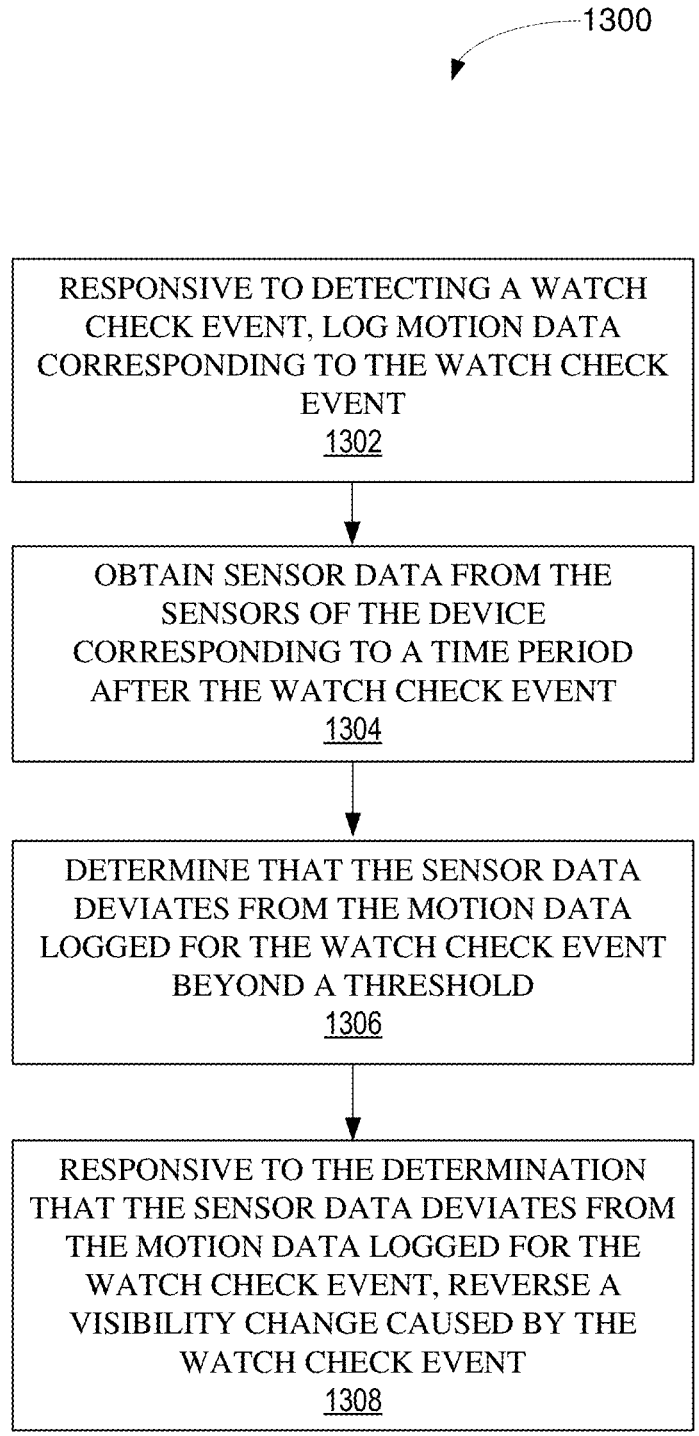
FIG. 13 is a flow chart illustrating a method for handling a dismissal user gesture, according to an example.

Once the watch check gesture detector detects a watch check event, the watch check gesture detector may allow the user to interact or otherwise interact with the screen in a number of ways. For example, in one embodiment, the watch check gesture detector may allow a user to reverse a visibility change caused by a watch check event responsive to detection of a dismissal gesture. Reversing the visibility change may involve the watch check gesture detector turning off an aspect of a display that was previously turned on by the watch check event or causing the display to return to a screen, metric, or content previously displayed before the watch check event. FIG. 13 is a flow chart illustrating a method 1300 for handling a dismissal user gesture, according to an example.

The method 1300 may begin at block 1302 when, responsive to detecting a watch check event, the watch check gesture detector may log motion data corresponding to the watch check event. For example, in one case, the watch check gesture detector may store the x and y values corresponding to when the watch check gesture detector detected the watch check event.

At block 1304, the watch check gesture detector may obtain or otherwise buffer sensor data from the sensors of the device corresponding to a time period after the watch check event. As described above, the sensor data may be motion data obtained from an accelerometer (e.g., a 3-axis accelerometer). Accordingly, the sensor data may represent acceleration of the device along 3 axes, labelled x, y, and z.

At block 1306, the watch check gesture detector may determine that the sensor data deviates from the motion data logged for the watch check event beyond a threshold. For example, one embodiment of the watch check gesture detector may compare the buffered sensor data with the logged motion data to determine whether the difference between the current value of the x-axis exceeds the x value associated with the watch check event beyond a threshold amount for a threshold number of samples. Additionally or alternatively, the watch check gesture detector may compare the buffered sensor data with the logged motion data to determine whether the difference between the current value of the y-axis exceeds the y value associated with the watch check event beyond a threshold amount for a threshold number of samples. The logged motion data may have a number of operations performed thereon to simplify the calculations performed by the watch check gesture detector, such as transforming to an absolute value, which may be performed on the y value.

At block 1308, responsive to the determination that the sensor data deviates from the motion data logged for the watch check event, the watch check gesture detector may reverse a visibility change caused by the watch check event. For example, where the display is turned on responsive to the watch check event, the watch check gesture detector may cause the display to be turned off. The same can be done for a back light that was turned on for the watch check event. Another example of reversing a visibility change is to change the screen, metric, or content displayed by the display to match the screen, metric, or content displayed prior to the watch check event.

Figure 14:
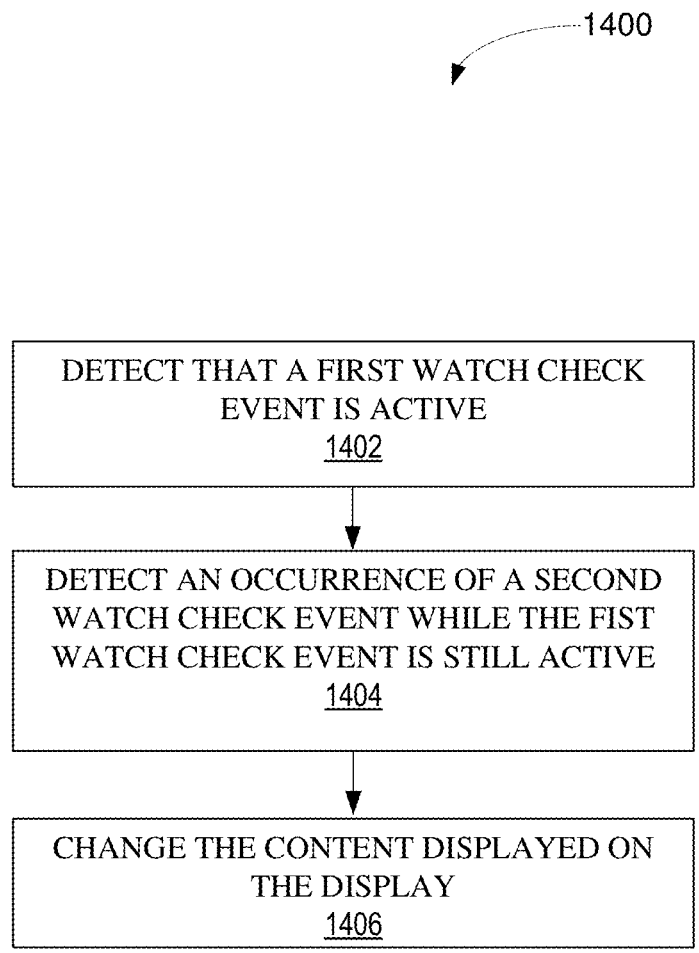
FIG. 14 is a flow chart illustrating a method for changing the content of a display based on further user interaction detected by the watch check gesture detector while a watch check event is still active.

Other embodiments may perform alternative or additional user operations while a watch check event is enabled. For example, some embodiments of the watch check gesture detector may allow a user to change the content of the screen depending on detecting user interactions with the device. For example, FIG. 14 is a flow chart illustrating a method 1400 for changing the content of a display based on further user interaction detected by the watch check gesture detector while a watch check event is still active.

The method 1400 may begin at 1402 when the watch check gesture detector detects that a first watch check event is active. This can be a watch check event triggered when the watch check gesture detector detects that the sensor data reflects that the device has undergone movement consistent with a user checking the display of the device if the device was worn of the user's wrist. Upon detecting the first watch check event, the watch check gesture detector may enable an aspect of the display of the device, such as turn on the display or turn on a back light of the display. When the aspect of the display is enabled, the display may display a first set of content (e.g., a time display, one or more metrics related to or otherwise derived from the activity, physiology, or environment of the user).

At block 1404, the watch check gesture detector may detect an occurrence of a second watch check event while the first watch check event is still active. Similar to block 1402, the second watch check event can be triggered when the watch check gesture detector detects that the sensor data reflects that the device has undergone movement consistent with a user checking the display of the device if the device was worn of the user's wrist. This movement can be the same or different from the movement that caused the first watch check event. By way of example and not limitation, the first watch check event may trigger based on detecting movement data indicative of the user bringing his wrist from their side to the front of their chest with the display of the device facing up towards the horizon. In comparison, the second watch check event may trigger based on detecting movement indicative of the user rotating their wrist from a starting position where the face of the display is moved from facing towards the horizon to facing towards the sky, as may occur during a hand-to-chest watch check event.

At block 1406, the watch check gesture detector may, responsive to the detection in block 1404, change the content displayed on the display. By way of example and not limitation, the watch check gesture detector may cause the display controller to update the display to display an additional metric being tracked by the device. In some cases, displaying the additional metric may cause the display controller to replace a metric that was being displayed on the display with the additional metric (e.g., a metric associated with an activity, physiological, or environmental metric; a location; an alert or notification from an secondary device paired to the device (e.g., phone, tablet, computer, and the like); a picture; an application running on the device, or any other suitable content).

In another embodiment, the non-running watch check gesture detector may be adapted to work in postures that are not upright—for instance, when lying down by adjusting the permissible orientation bounds after inferring that the user may be in bed. This may be inferred by observing an extended duration of little to no movement and an orientation in which gravity is projected mainly onto the x and/or z axes. A corresponding watch check may then be triggered when gravity is mainly projected on to the negative z axis (e.g., the display is facing downward), though other orientations may be permissible as well.

The logic described above with reference to FIGS. 1-14 employs decision rules such as watch check rules to determine that a watch check event has occurred. In other embodiments, this detection may be done using artificial neural networks, logistic regression, support vector machines, random forests, and other machine learning classifiers.

In another embodiment, the user may adjust the watch check detection algorithm's sensitivity. The setting may be adjustable on the device or a system in communication with the device (e.g., a website, an application on a mobile device such as a smartphone, etc.). Decreased sensitivity may take the form of tightening the bounds in the techniques previously described with reference to FIGS. 1-14. It may also take form in checking for a small window of time after a candidate watch check event where there is little motion and/or lack of reorientations. Both features are suggestive that the user is trying to read the display on the device. Extending the window would decrease sensitivity.

Figure 15:
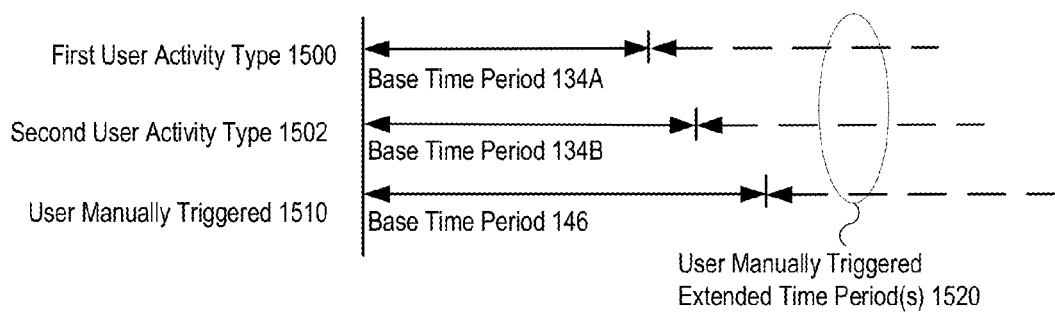
FIG. 15 illustrates the use of different base periods of time for an automatic display visibility change to be in effect based on the user's activity type, according to one embodiment.

FIG. 15 illustrates the use of different base periods of time for an automatic display visibility change to be in effect based on the user's activity type, according to one embodiment. FIG. 15 illustrates that the base time period 134A set for the first user activity type 1500 (e.g., set responsive to detection of a watch check gesture while the user is running) is shorter that the base time period 134B set for the second user activity 1502 (e.g., set responsive to detection of a watch check gesture while the user is performing a non-running activity), and the base time period 134B is shorter than the base time period 146 set response to the user manually triggering 1510 a change in the visibility of the display 150 to facilitate the user's viewing of the display 150 (e.g., by the user operating the electronic device using the user's hand of the user's arm opposite than that of the user's forearm on which the electronic device is being worn). Alternative embodiments may choose different base time periods (e.g., the same for all non-manually triggered). For example, in one embodiment, the base time period set responsive to detection of a watch check gesture while the user is running is within the range of 1-4 seconds (e.g., 4 seconds), the base time period set responsive to detection of a watch check gesture while the user is performing a non-running activity is within the range of 0.5-1 second (e.g., 1 second), and the base time period set responsive to a manually triggered change is 2-10 seconds (e.g., 4 seconds).

In another embodiment, after a watch check is triggered, the user may interact with the device with other motion gestures like taps, shakes, wrist rotations, etc. As an example, a watch check may cause the display to turn on showing a clock face. Subsequently, tapping on the device while the display is still on could cause the display to cycle through other data displays (e.g., time, pace, speed, distance, mile split, heart rate, clock, steps, floors, calories burned, and active minutes).

In one embodiment, after a watch check is triggered, the electronic device enters a mode where the electronic device senses audio and can respond to verbal commands from the user such as 'time', 'pace', 'speed', 'distance', 'mile split', 'heart rate', 'clock', 'steps', 'floors', 'calories burned', 'active minutes', and the like. In response to these verbal commands, the display may show the data corresponding to the command that was spoken. The device may stay in a speech recognition mode for a period of time (say, 5 seconds) or for the duration of the sensor data being indicative of the watch check gesture being held in place.

Figure 16:
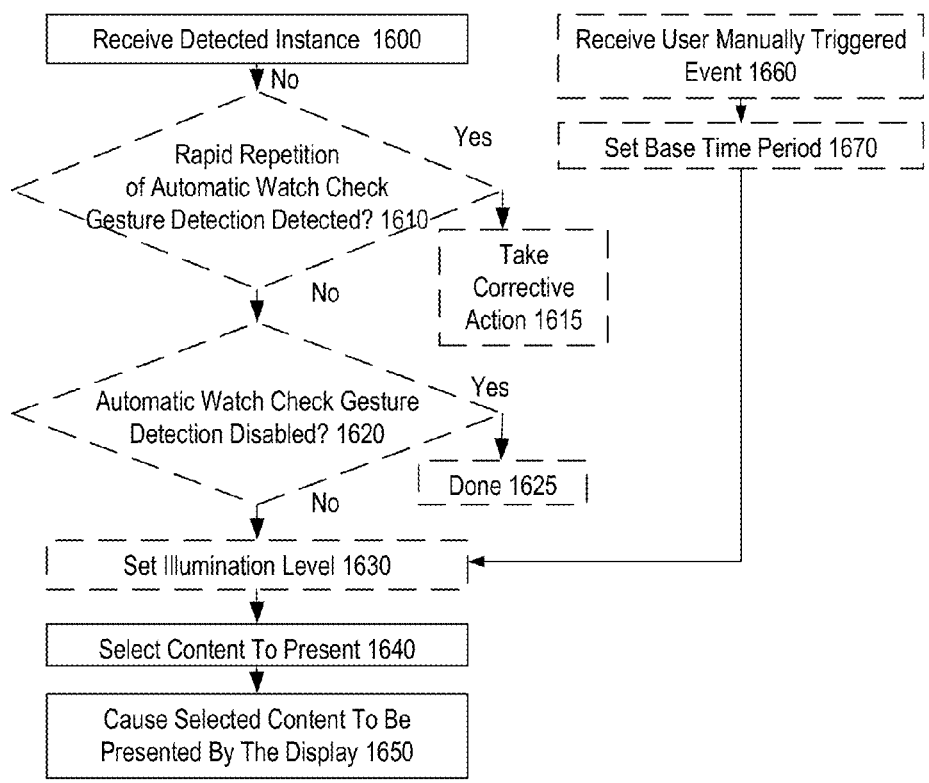
FIG. 16 is a flow diagram illustrating display visibility change control according to one embodiment.

FIG. 16 is a flow diagram illustrating display visibility change control according to one embodiment. With regard to FIG. 1, the flow of FIG. 16 may be performed by the display controller 140. FIG. 16 starts with the receipt of a detected instance (block 1600). From block 1600, control passes to optional block 1610.

In optional block 1610, it is determined if a rapid repetition of automatic watch check gestures has been detected. If so, control passes to optional block 1615 in which corrective action is taken; otherwise, control passes to optional block 1620. Blocks 1610 and 1615 may be performed by and in the manner previously described with reference to the rapid repetition of automatic watch check gesture detection detector 142.

In optional block 1620, it is determined if the automatic watch check gesture detection feature is disabled. If so, the flow is complete (block 1625); otherwise, control passes to the optional block 1630. Different embodiments may allow for the disabling of the automatic watch check gesture detection feature in different ways as described below.

In optional block 1630, the illumination level of the display is set and control passes to block 1640. Different embodiments may do so for different reasons and/or based upon current sensor data and/or mode of the electronic device. For instance, as described below, sensor data from an ambient light sensor may be used to set the illumination level higher in dim light and lower in brighter light.

In block 1640, the content to present is selected and control passes to block 1650. As described below in more detail, block 1640 includes the selection of a type of content to present in certain embodiments.

In block 1650, the display is caused to present the selected content. In an embodiment that supports different base time periods, the display would be caused to present the content for that period of time unless some other user interaction extended that time (and possibly caused the type of content to be change as previously described) or reduced that time (as described below with regard to automatic dismissal gesture detection).

Having described how watch check events can be detected, different embodiments may be implemented to select different content to present on the display based on different types of interaction. For example:

1. Under normal operation, the device may act like a watch and a watch check gesture triggers a display that shows the time, date, or a clock face.

2. For a display that is not easily viewable in dim light (e.g., an LCD display), a watch check gesture could automatically illuminate a backlight. This may be assisted by an ambient light sensor that determines the level of light near the user.

3. If the device is in a workout mode (or automatically detects that the user is exercising via elevated heart rate, step counts, or calorie burn), a watch check may present data that is relevant to that workout. For example, while running and doing heart rate training, a watch check may provide a display of the user's heart rate zone.

4. If the device provides a notification to the user (e.g., receives a text message and vibrates to notify the user), a watch check may present the data associated with the notification (e.g., the text message). Other examples of notifications are caller ID or meeting alert.

5. In combination with a location sensor (e.g., phone location services, GPS on device), the watch check may deactivate or become less sensitive. For example, if the user is determined to be in a movie theater or concert hall based on location, the watch check may turn off so that no false positives arise in a dimly lit public setting.

6. The device may have an "airplane mode", "sleep mode", "theater mode" or equivalent mode to disable the watch check gesture. For example, according to an example embodiment, the watch check gesture detector may determine that the user or wearer of the device is sleeping. Upon this determination, the watch check gesture detector may disable the various watch check rules. To enable the watch check rules, the watch check gesture detector may monitor the motion data to determine whether an enabling event has occurred. An example of an enabling event may be where the motion data reflects that the user has performed multiple watch check gestures within a time period (e.g., less than two seconds), an alarm is within a determinable time period (e.g., fifteen minutes), motion data reflects that the user is awake (and, consequently, turns off the sleep monitoring), the user has pressed a physical button on the device, or the like.

7. The device may automatically determine that the user is asleep (via motion and/or heart rate signals) and turn off or modify the behavior of the watch check detection.

8. If the device executes a wake up alarm (i.e., vibrates in the morning to wake up the user), the display may show relevant information like the time, date, weather, or sleep statistics.

9. The device may notify the user of a health alert—for example, buzzing when the user's blood pressure, stress level, heart rate, or blood glucose levels are outside of a target zone. In these instances, a watch check gesture may cause the display to present the relevant health data to the user.

10. After a goal celebration on the device (e.g., reaching 10,000 steps in a day), a watch check gesture may cause the display to present the user with the corresponding interactive experience (e.g., fireworks shown on the display).

11. As previously described, where the device has one or more buttons for the primary interaction mechanism, a watch check gesture may supplement this experience but with different length or presentation of data. For example, button presses on the electronic device will cycle through data displays for the user starting with the time, each display lasting for 4 seconds (or until the button is pushed again). A watch check may present a clock display for a shorter time, say, 1 second. This allows more tolerance for watch check false positives (for power consumption, because it is only on ¼ of the time).

12. The display that is presented to the user by a watch check may be user selected (e.g., heart rate instead of clock).

Figure 17:
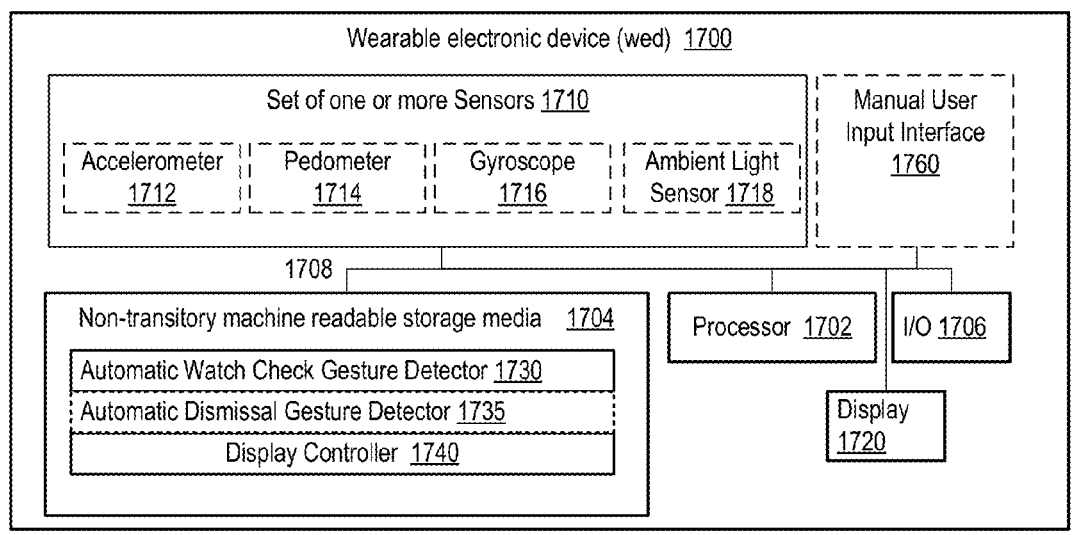
FIG. 17 is a block diagram of an electronic device to perform automatic display visibility changes responsive to user gestures according to one embodiment.

FIG. 17 is a block diagram of an electronic device to perform automatic display visibility changes responsive to user gestures according to one embodiment. Specifically, FIG. 17 illustrates a wearable electronic device (WED) 1700. The wearable electronic device 1700 includes, among other things not shown so as not to obscure the invention, an interconnect 1708 (e.g., one or more busses) coupling a set of one or more processors 1702, a non-transitory machine readable storage media 1704, an input/output (I/O) interface 1706, a set of one or more sensors 1710, a set of one or more displays 1720, and optionally a manual user input interface 1760. As with the set of sensors in FIG. 1, the set of sensors 1710 may include different sensors in different embodiments (e.g., an accelerometer 1712, a pedometer 1714, a gyroscope 1716, and an ambient light sensor 1718). The non-transitory machine readable storage media 1704 includes code to be executed by the set of processors 1702; that code including an automatic watch check gesture detector 1730 (to cause the electronic device to automatically cause changes in visibility of the display responsive to the user performing a watch check gesture as previously described herein), an automatic dismissal gesture detector 1735 (to cause the electronic device to automatically reverse automatic display visibility changes responsive to a user performing dismissal gestures as previously described herein), and a display controller 1740 (to cause the electronic device to operate in a manner similar to the display controller 140 previously described).

The I/O interface 1706 may implement wireless and/or wired communication using a variety of techniques including Bluetooth, RFID, Near-Field Communications (NFC), Zigbee, Ant, optical data transmission, wireless telephony (e.g., LTE), USB, etc.

The WED 1700 may collect one or more types of biometric data (data pertaining to physical characteristics of the human body, such as heartbeat, perspiration levels, etc. and/or data relating to the physical interaction of that body with the environment, such as accelerometer readings, gyroscope readings, etc.) from the set of sensors 1710 and/or external devices (such as an external heart rate monitor, e.g., a chest-strap heart rate monitor), and may then utilize the data in a variety of ways (e.g., make calculations based on such data, store the data and/or resulting calculations in the non-transitory machine readable storage media 1704), automatically act on such data and/or resulting calculation (automatic watch check and dismissal gesture detection), communicate such data and/or resulting calculations to another device via the I/O interface 1706 (e.g., to a another electronic device such as a smartphone, a tablet, a computer, a server over a wide-area network such as the Internet). As described above, the WED 1700 may also receive data from other electronic devices for storage and/or display on the display 1720 (e.g., notifications).

Figure 18:
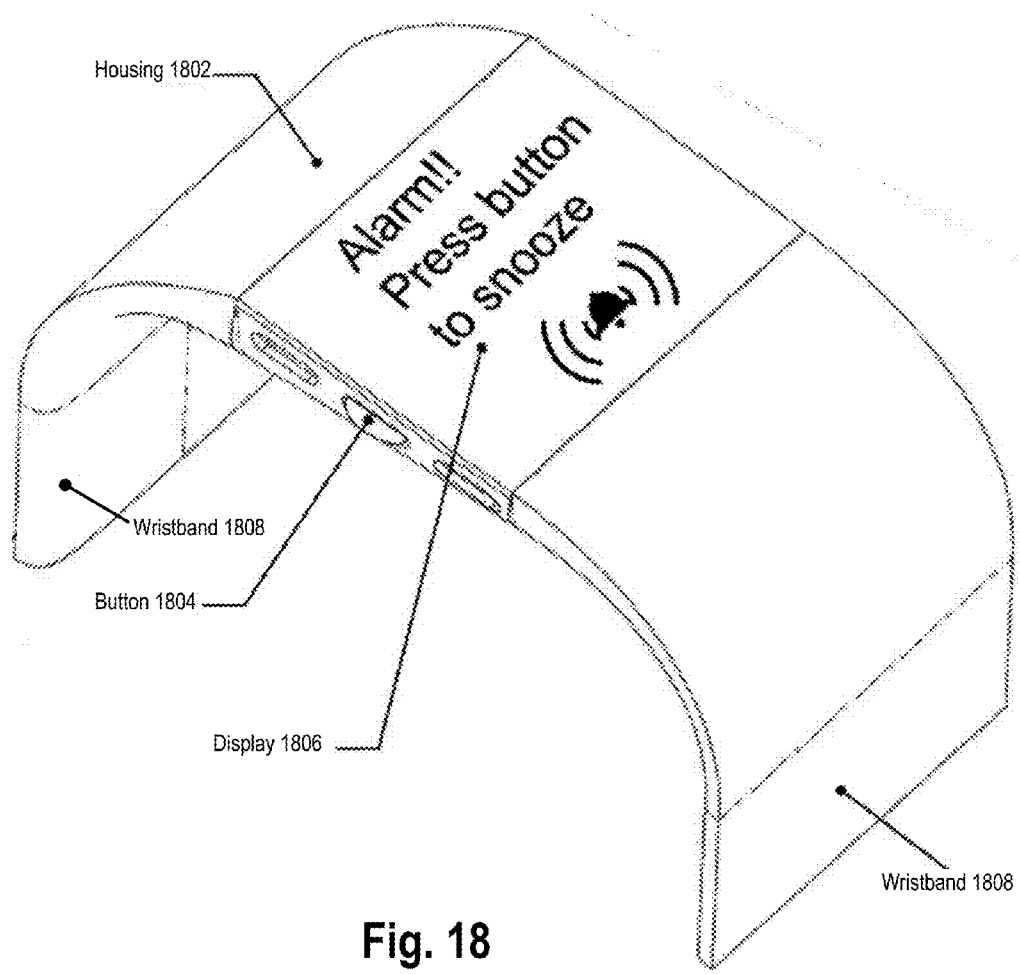
FIG. 18 is a block diagram of a wrist-mounted electronic device having a button, a display, and a wrist band to secure the electronic device to a user's forearm, according to one embodiment.

FIG. 18 is a block diagram of a wrist-mounted electronic device having a button, a display, and a wrist band to secure the electronic device to a user's forearm, according to one embodiment. Specifically, FIG. 18 depicts an electronic device (such as illustrated in FIGS. 1, 7, and/or 10) that may be worn on a person's forearm like a wristwatch. In FIG. 18, the electronic device has a housing 1802 that contains the electronics associated with the electronic device, a button 1804, and a display 1806 accessible/visible through the housing 1802. A wristband 1808 may be integrated with the housing 1802.

In addition to the display 1806 and button 1804, the electronic device may incorporate one or more types of user interfaces including but not limited to visual, auditory, touch/vibration, or combinations thereof. The WED 1700 may also provide haptic feedback through, for instance, the vibration of a motor. In some implementations, the set of sensors themselves may be used as part of the user interface, e.g., accelerometer sensors may be used to detect when a person taps the housing of the electronic device with a finger or other object and may then interpret such data as a user input for the purposes of controlling the electronic device. For example, double-tapping the housing of the electronic device may be recognized by the electronic device as a user input.

While FIG. 18 illustrates an implementation of the electronic device illustrated in FIGS. 1, 7, and 10, alternative embodiments may have other shapes and sizes adapted for coupling to the body or clothing of a user (e.g., secured to, worn, borne by, etc.) For example, the electronic device may be designed such that it may be inserted into, and removed from, a plurality of compatible cases/housings/holders, e.g., a wristband that may be worn on a person's forearm or a belt clip case that may be attached to a person's clothing. As used herein, the term "wristband" may refer to a band that is designed to fully or partially encircle a person's forearm near the wrist joint. The band may be continuous, e.g., without any breaks (it may stretch to fit over a person's hand or have an expanding portion similar to a dress watchband), or may be discontinuous, e.g., having a clasp or other connection allowing the band to be closed similar to a watchband or may be simply open, e.g., having a C-shape that clasps the wearer's wrist.

ALTERNATIVE EMBODIMENTS

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

In the following description, numerous specific details such as logic implementations, opcodes, resource partitioning/sharing/duplication implementations, types and interrelationships of system components, and logic partitioning/integration choices are set forth in order to provide a more thorough understanding of the present invention. It will be appreciated, however, by one skilled in the art that the invention may be practiced without such specific details. In other instances, control structures and full software instruction sequences have not been shown in detail in order not to obscure the invention. Those of ordinary skill in the art, with the included descriptions, will be able to implement appropriate functionality without undue experimentation.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As described above, this disclosure contemplates a number of different embodiments. By way of example and not limitation, at least the following embodiments are contemplated, consistent with this disclosure.

Embodiment #1Y

An apparatus comprising: a display; a set of sensors to provide sensor data during a first time period and a second time period; a set of processors coupled to the display and the set of sensors; a non-transitory machine readable storage medium coupled to the processor and having stored therein instructions, which when executed by the set of processors, cause the set of processors to: detect that the sensor data for the first time period matches a watch check rule; detect that the sensor data for the second time period matches a stability profile; and responsive to the detected matches, cause a change in visibility of the display.

Embodiment #1X

An apparatus comprising: a display; a set of sensors to provide sensor data during a first time period and a second time period; a set of processors coupled to the display and the set of sensors; a non-transitory machine readable storage medium coupled to the processor and having stored therein instructions, which when executed by the set of processors, cause the set of processors to: determine that the sensor data for the first time period matches a watch check rule; responsive to the detected match between the sensor data for the first time period and the first watch check rule, cause a change in visibility of the display; determine that the sensor data for the second time period matches the watch check rule; and responsive to the detected match between the sensor data for the second time period and the watch check rule, cause the display to update a screen with a different data type.

Embodiment #1W

An apparatus comprising: a display; a set of sensors to provide sensor data; a set of processors coupled to the display and the set of sensors; a non-transitory machine readable storage medium coupled to the processor and having stored therein instructions, which when executed by the set of processors, cause the set of processors to: detect, using the sensor data, that a first activity state (e.g., sleep activity) of a user is active; responsive to the detection that the first activity state of the user is active, disable a display controller from causing a change in visibility of the display based on sensor data from the set of sensors matching a watch check rule.

Embodiment #1A

An apparatus comprising: a display; a set of one or more sensors that provide sensor data; a set of one or more processors coupled to the display and the set of sensors; a non-transitory machine readable storage medium coupled to the processor and having stored therein instructions, which when executed by the set of processors, cause the device to: determine instances when the sensor data is indicative of the user, while performing a first type of activity, having made a first set of adjustments that the user would make to view a display of a wristwatch worn on the user's forearm during the user's performance of the first type of activity; determine instances when the sensor data is indicative of the user, while performing a second type of activity, having made a second set of adjustments that the user would make to view a display of a wristwatch worn on the user's forearm during the user's performance of the second type of activity; and cause changes in visibility of the display to facilitate the user's viewing of the display based on the instances.

Embodiment #2A

The apparatus of Embodiment #1A, wherein each of the changes in visibility of the display occur within five seconds of the user having made one of the first set of adjustments and the second set of adjustments.

Embodiment #3A

The apparatus of Embodiment #1A, wherein each of the changes in visibility of the display occur within half a second of the user having made one of the first set of adjustments and the second set of adjustments.

Embodiment #4A

The apparatus of Embodiment #1A, wherein each of the changes in visibility of the display occur within 400 milliseconds of the user having made one of the first set of adjustments and the second set of adjustments.

Embodiment #5A

The apparatus of Embodiment #1A, wherein each of the changes in visibility are for a base period of time.

Embodiment #6A

The apparatus of Embodiment #5A, wherein the base period of time for the instances when the sensor data is indicative of the user performing the first type of activity is different from the base period of time for the instances when the sensor data is indicative of the user performing the second type of activity.

Embodiment #7A

The apparatus of Embodiment #5A, wherein the base period of time for each of the changes in visibility is less than a base period of time for changes in visibility of the display to facilitate the user's viewing of the display triggered by the user operating the electronic device using the user's hand of the user's arm opposite than that of the user's forearm on which the electronic device is being worn.

Embodiment #8A

The apparatus of Embodiment #1A, wherein the set of sensors includes a three axis accelerometer.

Embodiment #9A

The apparatus of Embodiment #1A, wherein the sensor data upon which the determinations when the sensor data is indicative of the user, while performing the first type of activity, having made the first set of adjustments is from only a single three axis accelerometer.

Embodiment #10A

The apparatus of Embodiment #1A, wherein the second type of activity includes standing and walking.

Embodiment #11A

The apparatus of Embodiment #1A, wherein: the determination of instances when the sensor data is indicative of the user, while performing the first type of activity, having made the first set of adjustments includes a determination of when the sensor data reflects a number of preceding peaks in acceleration magnitude exceeds a threshold; and the determination of instances when the sensor data is indicative of the user, while performing the second type of activity, having made the second set of adjustments includes a determination of when the sensor data reflects a current acceleration magnitude is within a range.

Embodiment #12A

The apparatus of Embodiment #1A, wherein the instructions, when executed by the set of processors, also cause the device to: determine instances when the sensor data is indicative of the user, while performing a third type of activity, having made a third set of adjustments that the user would make to view a display of a wristwatch worn on the user's forearm during the user's performance of the third type of activity, wherein the first type of activity is running, the second type of activity includes walking, and the third type of activity is lying down.

Embodiment #13A

The apparatus of Embodiment #1A, wherein the changes in visibility of the display are also based on how many changes in the visibility of the display have been automatically caused within a time interval.

Embodiment #14A

The apparatus of Embodiment #1A, wherein the determinations are performed according to a current sensitivity level, wherein the current sensitivity level is decreased responsive to a threshold number of the automatically caused changes in the visibility of the display within a time interval.

Embodiment #15A

The apparatus of Embodiment #1A, wherein the changes in visibility of the display are one of turning on the display and turning on a back light.

Embodiment #16A

The apparatus of Embodiment #1A, wherein each of the changes in visibility is also based on a determination of an illumination level at which the display is to be set as part of that change.

Embodiment #17A

The apparatus of Embodiment #16A, wherein the electronic device includes an ambient light sensor, and wherein the determinations of the illumination level are based on data from the ambient light sensor.

Embodiment #18A

The apparatus of Embodiment #1A, wherein the automatic causation of changes in visibility of the display are also based on whether such changes are currently disabled.

Embodiment #19A

The apparatus of Embodiment #18A, wherein such changes are disabled responsive to one or more of a mode of the electronic device and a determination that the sensor data is indicative of the user being asleep.

Embodiment #20A

The apparatus of Embodiment #1A, wherein each of the changes in visibility is also based on a determination of a type of content to present on the display.

Embodiment #21A

The apparatus of Embodiment #20A, wherein the determinations of the type of content to present on the display are based on whether a goal was reached since a previous change in visibility of the display.

Embodiment #22A

The apparatus of Embodiment #20A, wherein the determinations of the type of content to present on the display are based on whether one of a notification and a health alert was detected since a previous change in visibility of the display.

Embodiment #23A

The apparatus of Embodiment #20A, wherein the type of content that is presented on the display is different for the instances when the sensor data is indicative of the user performing the first type of activity than for the instances when the sensor data is indicative of the user performing the second type of activity.

Embodiment #24A

The apparatus of Embodiment #23A, wherein the type of content presented on the display, for the instances when the sensor data is indicative of the user performing the first type of activity, is the user's heart rate zone.

Embodiment #25A

The apparatus of Embodiment #20A, wherein the determinations of the type of content to present include a selection from two or more of steps, pace, distance, floors, time, and heart rate.

Embodiment #26A

A method in an electronic device, worn on a user's forearm and having a display and having a set of one or more sensors that provide sensor data, to automatically cause changes in visibility of the display to facilitate the user's viewing of the display, the method comprising the steps of: automatically determining at a first time that the sensor data is indicative of the user, while performing a first type of activity, having made a first set of adjustments that the user would make to view a display of a wristwatch worn on the user's forearm during the user's performance of the first type of activity; automatically causing a change in visibility of the display responsive to the automatically determining at the first time; reversing the change in visibility of the display due to the expiration of a time period; automatically determining at a second time that the sensor data is indicative of the user, while performing a second type of activity, having made a second set of adjustments that the user would make to view a display of a wristwatch worn on the user's forearm during the user's performance of the second type of activity; and automatically causing the change in visibility in the display responsive to the automatically detecting at the second time.

Embodiment #27A

The method of Embodiment #26A, wherein each of the changes in visibility of the display occur within 400 milliseconds of the user having made one of the first set of adjustments and the second set of adjustments.

Embodiment #28A

The method of Embodiment #26A, wherein the sensor data upon which the automatically determining that the sensor data is indicative of the user, while performing the first type of activity, having made the first set of adjustments is only from a single three axis accelerometer.

Embodiment #29A

The method of Embodiment #26A, wherein each of the automatically causing the change in visibility include determining an illumination level at which the display is to be set as part of that change.

Embodiment #30A

The method of Embodiment #29A, wherein the electronic device includes an ambient light sensor, and wherein each of the determining the illumination level is based on data from the ambient light sensor.

Embodiment ##1B

An apparatus comprising: an electronic device to be worn on a user's forearm, the electronic device including: a display; a set of one or more sensors that provide sensor data; a set of one or more processors coupled to the display and the set of sensors; a non-transitory machine readable storage medium coupled to the processor and having stored therein instructions, which when executed by the set of processors, cause the device to: automatically determine instances when the sensor data is indicative of the user, while running, having slowed and having stabilized the electronic device to view the display in a manner a display of a wristwatch worn on the user's forearm would be viewed; and automatically cause changes in visibility of the display to facilitate the user's viewing of the display based on the instances.

Embodiment #2B

The apparatus of Embodiment #1B, wherein the determination of the instances when the sensor data is indicative of the user, while running, having slowed includes, determine instances when the sensor data reflects a dampening in acceleration.

Embodiment #3B

The apparatus of Embodiment #1B, wherein the determination of the instances when the sensor data is indicative of the user, while running, having slowed includes, determine instances when the sensor data reflects, a number of preceding peaks in acceleration magnitude exceed a threshold, and a current peak in acceleration magnitude is below a threshold and within a time interval of a most recent one of the preceding peaks.

Embodiment #4B

The apparatus of Embodiment #1B, wherein the determination of the instances when the sensor data is indicative of the user, while running, having stabilized the electronic device to view the display in the manner the display of a wristwatch worn on the user's forearm would be viewed includes, determine instances when the sensor data reflects a current acceleration magnitude along the Y axis is within a threshold of a current acceleration magnitude along the X axis and Z axis.

Embodiment #5B

The apparatus of Embodiment #1B, wherein the determination of the instances when the sensor data is indicative of the user, while running, having slowed and having stabilized the electronic device to view the display in the manner the display of a wristwatch worn on the user's forearm would be viewed includes, determine instances when the sensor data reflects, a dampening in acceleration; and a current acceleration magnitude along the Y axis is within a threshold of a current acceleration magnitude along the X axis and Z axis.

Embodiment #6B

The apparatus of Embodiment #1B, wherein the determination of the instances when the sensor data is indicative of the user, while running, having slowed and having stabilized the electronic device to view the display in the manner the display of a wristwatch worn on the user's forearm would be viewed includes, determine the instances when the sensor data reflects, a number of preceding peaks in acceleration magnitude exceed a threshold, a current peak in acceleration magnitude is below a threshold and within a time interval of a most recent one of the preceding peaks, a current acceleration magnitude along the Y axis is within a threshold of a current acceleration magnitude along the X axis and Z axis; and a threshold percentage of a last threshold number of peaks in acceleration magnitude exceed a threshold acceleration magnitude.

Embodiment #7B

The apparatus of Embodiment #1B, wherein each of the changes in visibility of the display occur within five seconds of the user having slowed and having stabilized the electronic device to view the display in the manner a display of a wristwatch worn on the user's forearm would be viewed.

Embodiment #8B

The apparatus of Embodiment #1B, wherein each of the changes in visibility of the display occur within half a second of the user having slowed and having stabilized the electronic device to view the display in the manner a display of a wristwatch worn on the user's forearm would be viewed.

Embodiment #9B

The apparatus of Embodiment #1B, wherein each of the changes in visibility of the display occur within 400 milliseconds of the user having slowed and having stabilized the electronic device to view the display in the manner a display of a wristwatch worn on the user's forearm would be viewed.

Embodiment #10B

The apparatus of Embodiment #1B, wherein each of the changes in visibility is for a base period of time, and wherein the base period of time for each of the changes in visibility is less than a base period of time for changes in visibility of the display to facilitate the user's viewing of the display triggered by the user operating the electronic device using the user's hand of the user's arm opposite than that of the user's forearm on which the electronic device is being worn.

Embodiment #11B

The apparatus of Embodiment #1B, wherein the set of sensors includes a three axis accelerometer.

Embodiment #12B

The apparatus of Embodiment #1B, wherein the sensor data upon which the determination of instances is based is only from a single three axis accelerometer.

Embodiment #13B

The apparatus of Embodiment #1B, wherein the changes in visibility of the display are one of turning on the display and turning on a back light.

Embodiment #14B

The apparatus of Embodiment #1B, wherein each of the changes in visibility is also based on a determination of an illumination level at which the display is to be set as part of that change.

Embodiment #15B

The apparatus of Embodiment #14B, wherein the electronic device includes an ambient light sensor, and wherein the determinations of the illumination level are based on data from the ambient light sensor.

Embodiment #16B

The apparatus of Embodiment #1B, wherein the automatic causation of changes in visibility of the display are also based on whether such changes are currently disabled.

Embodiment #17B

The apparatus of Embodiment #1B, wherein each of the changes in visibility is also based on a determination of a type of content to present on the display.

Embodiment #18B

The apparatus of Embodiment #17B, wherein the determinations of the type of content to present on the display are based on whether a goal was reached since a previous change in visibility of the display.

Embodiment #19B

The apparatus of Embodiment #17B, wherein the determinations of the type of content to present on the display are based on whether one of a notification and a health alert was detected since a previous change in visibility of the display.

Embodiment #20B

The apparatus of Embodiment #17B, wherein the determinations of the type of content to present include a selection from two or more of steps, a pace, a distance, a time, a heart rate, a heart rate zone, a goal reached, a notification, and a health alert.

Embodiment #21B

A method in an electronic device, worn on a user's forearm and having a display and having a set of one or more sensors that provide sensor data, to automatically cause changes in visibility of the display to facilitate the user's viewing of the display, the method comprising the steps of: automatically determining that the sensor data is indicative of the user, while running, having slowed and having stabilized the electronic device to view the display in a manner a display of a wristwatch worn on the user's forearm would be viewed; and automatically causing a change in visibility of the display responsive to the automatically determining.

Embodiment #22B

The method of Embodiment #21B, wherein the automatically determining that the sensor data is indicative of the user, while running, having slowed includes, determining that the sensor data reflects a dampening in acceleration.

Embodiment #23B

The method of Embodiment #21B, wherein the automatically determining that the sensor data is indicative of the user, while running, having slowed includes, determining that the sensor data reflects, a number of preceding peaks in acceleration magnitude exceed a threshold, and a current peak in acceleration magnitude is below a threshold and within a time interval of a most recent one of the preceding peaks.

Embodiment #24B

The method of Embodiment #21B, wherein the automatically determining that the sensor data is indicative of the user, while running, having stabilized the electronic device to view the display in the manner the display of a wristwatch worn on the user's forearm would be viewed includes, determining that the sensor data reflects a current acceleration magnitude along the Y axis is within a threshold of a current acceleration magnitude along the X axis and Z axis.

Embodiment #25B

The method of Embodiment #21B, wherein the automatically determining that the sensor data is indicative of the user, while running, having slowed and having stabilized the electronic device to view the display in the manner the display of a wristwatch worn on the user's forearm would be viewed includes, determining that the sensor data reflects, a dampening in acceleration; and a current acceleration magnitude along the Y axis is within a threshold of a current acceleration magnitude along the X axis and Z axis.

Embodiment #26B

The method of Embodiment #21B, wherein the automatically determining that the sensor data is indicative of the user, while running, having slowed and having stabilized the electronic device to view the display in the manner the display of a wristwatch worn on the user's forearm would be viewed includes, determining that the sensor data reflects, a number of preceding peaks in acceleration magnitude exceed a threshold, a current peak in acceleration magnitude is below a threshold and within a time interval a most recent one of the preceding peaks, a current acceleration magnitude along the Y axis is within a threshold of a current acceleration magnitude along the X axis and Z axis and; a threshold percentage of a last threshold number of peaks in acceleration magnitude exceed a threshold acceleration magnitude.

Embodiment #27B

The method of Embodiment #21B, wherein the change in visibility of the display occurs within 400 milliseconds of the user having slowed and having stabilized the electronic device to view the display in the manner the display of a wristwatch worn on the user's forearm would be viewed.

Embodiment #28B

The method of Embodiment #21B, wherein the sensor data upon which the automatically determining is based is only from a single three axis accelerometer.

Embodiment #29B

The method of Embodiment #21B, wherein the changes in visibility includes determining an illumination level at which the display is to be set.

Embodiment #30B

The method of Embodiment #29B, wherein the electronic device includes an ambient light sensor, and wherein the determining the illumination level is based on data from the ambient light sensor.

Embodiment #1C

An apparatus comprising: an electronic device to be worn on a user's forearm, the electronic device including: a display; a set of one or more sensors that provide sensor data; a set of one or more processors coupled to the display and the set of sensors; a non-transitory machine readable storage medium coupled to the processor and having stored therein instructions, which when executed by the set of processors, cause the device to: automatically determine instances when the sensor data meets a set of requirements indicative of the user performing a watch check gesture, wherein the set of requirements includes the sensor data reflecting that, the display is oriented one of upward and tilted toward the user's face, and during a time interval there was a change in acceleration magnitude along a z axis exceeding a first threshold and a change in acceleration magnitude along an x axis exceeding a second threshold for a third threshold percentage of that sensor data; and automatically cause changes in visibility of the display based on the instances.

Embodiment #2C

The apparatus of Embodiment #1C, wherein the set of requirements includes the sensor data also reflecting that a current acceleration magnitude is within a range.

Embodiment #3C

The apparatus of Embodiment #1C, wherein the set of requirements includes the sensor data also reflecting that a current acceleration magnitude along the y axis is within a threshold of a current acceleration magnitude along the x axis and z axis.

Embodiment #4C

The apparatus of Embodiment #1C, wherein the set of requirements includes the sensor data also reflecting that, a current acceleration magnitude is within a range; and a current acceleration magnitude along the Y axis is within a threshold of a current acceleration magnitude along the X axis and Z axis.

Embodiment #5C

The apparatus of Embodiment #1C, wherein each of the changes in visibility of the display occur within five seconds of the user having performed the watch check gesture.

Embodiment #6C

The apparatus of Embodiment #1C, wherein each of the changes in visibility of the display occur within half a second of the user having performed the watch check gesture.

Embodiment #7C

The apparatus of Embodiment #1C, wherein each of the changes in visibility of the display occur within 400 milliseconds of the user having performed the watch check gesture.

Embodiment #8C

The apparatus of Embodiment #1C, wherein each of the changes in visibility is for a base period of time, and wherein the base period of time for each of the changes in visibility is less than a base period of time for changes in visibility of the display to facilitate the user's viewing of the display triggered by the user operating the electronic device using the user's hand of the user's arm opposite than that of the user's forearm on which the electronic device is being worn.

Embodiment #9C

The apparatus of Embodiment #1C, wherein the set of sensors includes a three axis accelerometer.

Embodiment #10C

The apparatus of Embodiment #1C, wherein the sensor data upon which the determination of instances is based is only from a single three axis accelerometer.

Embodiment #11C

The apparatus of Embodiment #1C, wherein the set of sensors includes a pedometer, and wherein the determination of the instances includes lowering a current sensitivity level of at least one of the set of requirements while the pedometer indicates that the user is walking.

Embodiment #12C

The apparatus of Embodiment #1C, wherein the determination of the instances includes, a determination of whether the sensor data reflects that the user is walking; and a determination of the third threshold based on whether the user is walking.

Embodiment #13C

The apparatus of Embodiment #1C, wherein the changes in visibility of the display are also based on how many changes in the visibility of the display have been automatically caused within a time interval.

Embodiment #14C

The apparatus of Embodiment #1C, wherein the determination of instances are performed according to a current sensitivity level, wherein the current sensitivity level is decreased responsive to a threshold number of the automatically caused changes in the visibility of the display within a time interval.

Embodiment #15C

The apparatus of Embodiment #1C, wherein the changes in visibility of the display are one of turning on the display and turning on a back light.

Embodiment #16C

The apparatus of Embodiment #1C, wherein each of the changes in visibility is also based on a determination of an illumination level at which the display is to be set as part of that change.

Embodiment #17C

The apparatus of Embodiment #16C, wherein the electronic device includes an ambient light sensor, and wherein the determinations of the illumination level are based on data from the ambient light sensor.

Embodiment #18C

The apparatus of Embodiment #1C, wherein the automatic causation of changes in visibility of the display are also based on whether such changes are currently disabled.

Embodiment #19C

The apparatus of Embodiment #18C, wherein such changes are disabled responsive to one or more of a mode of the electronic device and a determination that the sensor data is indicative of the user being asleep.

Embodiment #20C

The apparatus of Embodiment #1C, wherein each of the changes in visibility is also based on a determination of a type of content to present on the display.

Embodiment #21C

The apparatus of Embodiment #20C, wherein the determinations of the type of content to present on the display are based on whether a goal was reached since a previous change in visibility of the display.

Embodiment #22C

The apparatus of Embodiment #20C, wherein the determinations of the type of content to present on the display are based on whether one of a notification and a health alert was detected since a previous change in visibility of the display.

Embodiment #23C

The apparatus of Embodiment #20C, wherein the determinations of the type of content to present include a selection from two or more of steps, a pace, a distance, a time, a heart rate, a heart rate zone, a goal reached, a notification, and a health alert.

Embodiment #24C

A method in an electronic device, worn on a user's forearm and having a display and having a set of one or more sensors that provide sensor data, to automatically cause changes in visibility of the display to facilitate the user's viewing of the display, the method comprising the steps of: automatically determining instances when the sensor data meets a set of requirements indicative of the user performing a watch check gesture, wherein the set of requirements includes the sensor data reflecting that, the display is oriented one of upward and tilted toward the user's face, and during a time interval there was a change in acceleration magnitude along a Z axis exceeding a first threshold and a change in acceleration magnitude along an X axis exceeding a second threshold; and automatically causing changes in visibility of the display to facilitate the user's viewing of the display based on the instances.

Embodiment #25C

The method of Embodiment #24C, wherein the set of requirements includes the sensor data also reflecting that a current acceleration magnitude is within a range.

Embodiment #26C

The method of Embodiment #24C, wherein the set of requirements includes the sensor data also reflecting that a current acceleration magnitude along the y axis is within a threshold of a current acceleration magnitude along the x axis and z axis.

Embodiment #27C

The method of Embodiment #24C, wherein the set of requirements includes the sensor data also reflecting that, a current acceleration magnitude is within a range; and a current acceleration magnitude along the y axis is within a threshold of a current acceleration magnitude along the x axis and z axis.

Embodiment #28C

The method of Embodiment #24C, wherein each of the changes in visibility of the display occur within 400 milliseconds of the user having performed the watch check gesture.

Embodiment #29C

The method of Embodiment #24C, wherein the set of sensors includes a pedometer, and wherein the determination of the instances includes lowering a current sensitivity level of at least one of the set of requirements while the pedometer indicates that the user is walking.

Embodiment #30C

The method of Embodiment #24C, wherein the changes in visibility of the display are also based on how many changes in the visibility of the display have been automatically caused within a time interval.

Embodiment #1D

An apparatus comprising: an electronic device to be worn on a user's forearm, the electronic device including: a display; a set of one or more sensors that provide sensor data; a set of one or more processors coupled to the display and the set of sensors; a non-transitory machine readable storage medium coupled to the processor and having stored therein instructions, which when executed by the set of processors, cause the device to: automatically cause changes in visibility of the display to facilitate viewing of the display by the user when the sensor data is indicative of the user having made adjustments to view the display; automatically determine instances when the sensor data is indicative of the user having made a dismissal gesture while one of the automatically caused changes in visibility of the display is currently active; and automatically reverse, responsive to the instances, the ones of the automatically caused changes in visibility of the display that are currently active during the instances.

Embodiment #2D

The apparatus of Embodiment #1D, wherein the determination of the instances includes: determine instances when the sensor data is indicative of the user, while performing a first type of activity, having made the dismissal gesture during the user's performance of the first type of activity; and determine instances when the sensor data is indicative of the user, while performing a second type of activity, having made the dismissal gesture during the user's performance of the second type of activity.

Embodiment #3D

The apparatus of Embodiment #2D, wherein the determination of the instances when the sensor data is indicative of the user, while performing the first type of activity, having made the dismissal gesture during the user's performance of the first type of activity includes, determine instances when the sensor data reflects that a number of peaks in acceleration magnitude exceed a threshold.

Embodiment #4D

The apparatus of Embodiment #2D, wherein the determination of the instances when the sensor data is indicative of the user, while performing the first type of activity, having made the dismissal gesture during the user's performance of the first type of activity includes, determine instances when the sensor data reflects that subsequent acceleration peaks exceed a threshold.

Embodiment #5D

The apparatus of Embodiment #2D, wherein the determination of the instances when the sensor data is indicative of the user, while performing the first type of activity, having made the dismissal gesture during the user's performance of the first type of activity includes, determine instances when the sensor data reflects that a current acceleration magnitude along the Y axis is normal relative to a current acceleration magnitude along the X axis and Z axis.

Embodiment #6D

The apparatus of Embodiment #2D, wherein the determination of the instances when the sensor data is indicative of the user, while performing the first type of activity, having made the dismissal gesture during the user's performance of the first type of activity includes, determine instances when the sensor data reflects that a ratio of a current acceleration magnitude along the X axis and Z axis to a current acceleration magnitude along the X axis, the Y axis, and the Z axis falls below a threshold.

Embodiment #7D

The apparatus of Embodiment #2D, wherein the determination of the instances when the sensor data is indicative of the user, while performing the second type of activity, having made the dismissal gesture during the user's performance of the second type of activity includes, determine instances when the sensor data reflects that a current acceleration magnitude is outside a range.

Embodiment #8D

The apparatus of Embodiment #2D, wherein the determination of the instances when the sensor data is indicative of the user, while performing the second type of activity, having made the dismissal gesture during the user's performance of the second type of activity includes, determine instances when the sensor data reflects that the user actively reoriented the display relative to a reorientation that triggered the automatically caused change in visibility of the display that is currently active.

Embodiment #9D

The apparatus of Embodiment #2D, wherein the first type of activity is running and the second type of activity excludes running.

Embodiment #10D

The apparatus of Embodiment #2D, wherein the second type of activity includes standing and walking.

Embodiment #11D

The apparatus of Embodiment #1D, wherein each of the automatically caused changes in visibility are for a base period of time, wherein the base period of time for each of the automatically caused changes in visibility is less than a base period of time for changes in visibility of the display to facilitate the user's viewing of the display triggered by the user operating the electronic device using the user's hand of the user's arm opposite than that of the user's forearm on which the electronic device is being worn.

Embodiment #12D

The apparatus of Embodiment #1D, wherein the set of sensors includes a three axis accelerometer.

Embodiment #13D

The apparatus of Embodiment #1D, wherein the sensor data upon which the determinations are based is only from a single three axis accelerometer.

Embodiment #14D

The apparatus of Embodiment #1D, wherein the automatic reversals are one of turning off the display and turning off a back light.

Embodiment #15D

The apparatus of Embodiment #1D, wherein each of the automatically caused changes in visibility of the display includes a determination of a type of content to present on the display.

Embodiment #16D

The apparatus of Embodiment #15D, wherein the determinations of the type of content to present on the display are based on whether a goal was reached since a previous change in visibility of the display.

Embodiment #17D

The apparatus of Embodiment #15D, wherein the determinations of the type of content to present on the display are based on whether one of a notification and a health alert was detected since a previous change in visibility of the display.

Embodiment #18D

The apparatus of Embodiment #15D, wherein the determinations of the type of content to present include a selection from two or more of steps, pace, distance, time, heart rate, heart rate zone, goal reached, notification, and health alert.

Embodiment #19D

A method in an electronic device, worn on a user's forearm and having a display and having a set of one or more sensors that provide sensor data, to automatically cause changes in visibility of the display to facilitate the user's viewing of the display, the method comprising the steps of: automatically causing a change in visibility of the display to facilitate viewing of the display by the user responsive to sensor data being indicative of the user having made adjustments to view the display; automatically determining that the sensor data is indicative of the user having made a dismissal gesture while the automatically caused change in visibility of the display is active; and automatically reversing the automatically caused change in visibility of the display responsive to the automatically determining.

Embodiment #20D

The method of Embodiment #19D, wherein the automatically determining is based on which one of a plurality of activity types that the electronic device has detected that the user is currently performing.

Embodiment #21D

The method of Embodiment #20D, wherein a first of the plurality of activity types is running and a second of the plurality of activity types excludes running.

Embodiment #22D

The method of Embodiment #20D, wherein one of the plurality of activity types includes standing and walking.

Embodiment #23D

The method of Embodiment #19D, wherein the automatically determining includes, determining that the sensor data reflects that a number of peaks in acceleration magnitude exceed a threshold.

Embodiment #24D

The method of Embodiment #19D, wherein the automatically determining includes, determining that the sensor data reflects that subsequent accelerometer peaks exceed a threshold.

Embodiment #25D

The method of Embodiment #19D, wherein the automatically determining includes, determining that the sensor data reflects that a ratio of a current acceleration magnitude along the x axis and z axis to a current acceleration magnitude along the x axis, the y axis, and the z axis falls below a threshold.

Embodiment #26D

The method of Embodiment #19D, wherein the automatically determining includes, determining that the sensor data reflects that a current acceleration magnitude is outside a range.

Embodiment #27D

The method of Embodiment #19D, wherein the automatically determining includes, determining that the sensor data reflects that the user actively reoriented the display relative to a reorientation that triggered the automatically caused change in visibility of the display.

Embodiment #28D

The method of Embodiment #19D, wherein the sensor data upon which the automatically determining is based is only from a single three axis accelerometer.

Embodiment #29D

The method of Embodiment #19D, wherein automatically reversing includes one of turning off the display and turning off a back light.

Embodiment #30D

The method of Embodiment #19D, wherein the automatically causing a change in visibility of the display includes determining a type of content to present on the display.

While the flow diagrams in the figures show a particular order of operations performed by certain embodiments, it should be understood that such order is exemplary (e.g., alternative embodiments may perform the operations in a different order, combine certain operations, overlap certain operations, etc.).

Bracketed text and blocks with dashed borders (e.g., large dashes, small dashes, dot-dash, and dots) may be used herein to illustrate optional operations that add additional features to embodiments. However, such notation should not be taken to mean that these are the only options or optional operations, and/or that blocks with solid borders are not optional in certain embodiments.

In the following description and claims, the terms "coupled" and "connected," along with their derivatives, may be used. It should be understood that these terms are not intended as synonyms for each other. "Coupled" is used to indicate that two or more elements, which may or may not be in direct physical or electrical contact with each other, co-operate or interact with each other. "Connected" is used to indicate the establishment of communication between two or more elements that are coupled with each other.

The operations in the flow diagrams will be described with reference to the exemplary embodiments of the other figures. However, it should be understood that the operations of the flow diagrams can be performed by embodiments other than those discussed with reference to the other figures, and the embodiments discussed with reference to these other figures can perform operations different than those discussed with reference to the flow diagrams.

An electronic device stores and transmits (internally and/or with other electronic devices over a network) code (which is composed of software instructions and which is sometimes referred to as computer program code or a computer program) and/or data using machine-readable media (also called computer-readable media), such as machine-readable storage media (e.g., magnetic disks, optical disks, read only memory (ROM), flash memory devices, phase change memory) and machine-readable transmission media (also called a carrier) (e.g., electrical, optical, radio, acoustical or other form of propagated signals—such as carrier waves, infrared signals). Thus, an electronic device (e.g., a computer) includes hardware and software, such as a set of one or more processors coupled to one or more machine-readable storage media to store code for execution on the set of processors and/or to store data. For instance, an electronic device may include non-volatile memory containing the code since the non-volatile memory can persist code/data even when the electronic device is turned off (when power is removed), and while the electronic device is turned on that part of the code that is to be executed by the processor(s) of that electronic device is typically copied from the slower non-volatile memory into volatile memory (e.g., dynamic random access memory (DRAM), static random access memory (SRAM)) of that electronic device. Typical electronic devices also include a set of one or more physical network interface(s) to establish network connections (to transmit and/or receive code and/or data using propagating signals) with other electronic devices. One or more parts of an embodiment may be implemented using different combinations of software, firmware, and/or hardware.

What is claimed is:

1. An apparatus comprising:
   a display;
   a set of one or more sensors configured to generate sensor data during a first time period and a second time period;
   a set of one or more processors coupled to the display and the set of one or more sensors; and
   a non-transitory machine readable storage medium coupled to the set of one or more processors and having stored therein a watch check gesture detector for receiving the sensor data, the watch check gesture detector comprising a watch check rule for causing a change to the display, wherein the watch check rule includes data or logic that represents one or more patterns of movement indicative of a user of the apparatus checking the display,
   wherein the storage medium further comprises instructions that, when executed by the set of one or more processors, cause the set of one or more processors to:
      detect, using the sensor data, that the user is performing a particular type of activity;
      enable the watch check rule based on the detection;
      determine, based on the sensor data generated during the first time period and while a first activity metric is displayed on the display, that the user has made a bodily adjustment matching the one or more patterns of movement indicative of the user checking the display such that the watch check rule is satisfied;

in response to determining that the watch check rule is satisfied, cause a first change to the display, the first change causing the display displaying the first activity metric to display a second activity metric different from the first activity metric and indicative of the user's performance with respect to the particular type of activity;

log first accelerometer data extracted from the sensor data generated during the first time period, the first accelerometer data comprising a first x-axis value and a first y-axis value;

extract second accelerometer data from the sensor data generated during the second time period, the second accelerometer data comprising a second x-axis value and a second y-axis value;

determine whether the second x-axis value of the second accelerometer data exceeds the first x-axis value of the logged first accelerometer data by a first threshold amount;

determine whether the second y-axis value of the second accelerometer data exceeds the first y-axis value of the logged first accelerometer data by a second threshold amount; and in response to determining that (i) the second x-axis value exceeds the first x-axis value by the first threshold amount and (ii) the second y-axis value exceeds the first y-axis value by the second threshold amount, cause a second change to the display, the second change causing the display displaying the second activity metric to display the first activity metric.

2. The apparatus of claim 1, wherein the set of one or more sensors is further configured to generate sensor data during a third time period, and the instructions, when executed by the set of one or more processors, further cause the set of one or more processors to calculate the second activity metric from the sensor data generated during the third time period.

3. The apparatus of claim 2, wherein the sensor data generated during the third time period includes third accelerometer data, and the second activity metric is a step count.

4. The apparatus of claim 2, wherein the second activity metric is at least one of a time, a pace, a speed, a distance, a mile split, a heart rate, a clock, a step count, a floor count, an estimation of calories burned, or an active minute count.

5. The apparatus of claim 1, wherein the instructions, when executed by the set of one or more processors, further cause the set of one or more processors to determine that the second x-axis value exceeds the first x-axis value by the first threshold amount when the second x-axis value exceeds the first x-axis value by the first threshold amount for a first threshold number of samples, and to determine that the second y-axis value exceeds the first y-axis value by the second threshold amount when the second y-axis value exceeds the first y-axis value by the second threshold amount for a second threshold number of samples.

6. The apparatus of claim 1, wherein the instructions, when executed by the set of one or more processors, further cause the set of one or more processors to transform each of one or more of the first and second x-axis values and the first and second y-axis values to an absolute value.

7. A non-transitory machine readable storage medium storing therein a watch check detector for receiving sensor data generated by one or more sensors of a wearable electronic device, the watch check gesture detector comprising a watch check rule for causing a change to a display of the wearable electronic device, wherein the watch check rule includes data or logic that represents one or more patterns of movement indicative of a user of the wearable electronic device checking the display, wherein the storage medium further comprises instructions that, when executed by one or more processors, cause the one or more processors to:

detect, using the sensor data, that the user is performing a particular type of activity;

enable the watch check rule based on the detection;

determine, based on sensor data generated by the one or more sensors during a first time period and while a first content is displayed on the display, that the user has made a bodily adjustment matching the one or more patterns of movement indicative of the user checking the display such that the watch check rule is satisfied;

in response to determining that the watch check rule is satisfied, cause a first change to the display, the first change causing the display displaying the first content to display a first activity metric different from the first content and indicative of the user's performance with respect to the particular type of activity;

log first accelerometer data extracted from the sensor data generated during the first time period, the first accelerometer data comprising a first x-axis value and a first y-axis value;

extract second accelerometer data from sensor data generated during a second time period, the second accelerometer data comprising a second x-axis value and a second y-axis value;

determine whether the second x-axis value of the second accelerometer data exceeds the first x-axis value of the logged first accelerometer data by a first threshold amount;

determine whether the second y-axis value of the second accelerometer data exceeds the first y-axis value of the logged first accelerometer data by a second threshold amount; and in response to determining that (i) the second x-axis value exceeds the first x-axis value by the first threshold amount and (ii) the second y-axis value exceeds the first y-axis value by the second threshold amount, cause a second change to the display, the second change causing the display displaying the first activity metric to display the first content.

8. The non-transitory machine readable storage medium of claim 7, wherein causing the first change includes causing the display displaying a second activity metric different from the first activity metric to display the first activity metric.

9. The non-transitory machine readable storage medium of claim 7, wherein the instructions, when executed by the one or more processors, further cause the one or more processors to:

obtain sensor data generated by the one or more sensors during a third time period; and calculate the first activity metric from the sensor data generated during the third time period.

10. The non-transitory machine readable storage medium of claim 9, wherein the sensor data generated during the third time period includes third accelerometer data, and the first activity metric is a step count.

11. The non-transitory machine readable storage medium of claim 9, wherein the first activity metric is at least one of a time, a pace, a speed, a distance, a mile split, a heart rate, a clock, a step count, a floor count, an estimation of calories burned, or an active minute count.

12. The non-transitory machine readable storage medium of claim 7, wherein the instructions, when executed by the one or more processors, further cause the one or more processors to determine that the second x-axis value exceeds the first x-axis value by the first threshold amount when the second x-axis value exceeds the first x-axis value by the first threshold amount for a first threshold number of samples, and to determine that the second y-axis value exceeds the first y-axis value by the second threshold amount when the second y-axis value exceeds the first y-axis value by the second threshold amount for a second threshold number of samples.

13. The non-transitory machine readable storage medium of claim 7, wherein the instructions, when executed by the one or more processors, further cause the one or more processors to transform each of one or more of the first and second x-axis values and the first and second y-axis values to an absolute value.

14. The non-transitory machine readable storage medium of claim 7, wherein the second change to the display is causing the display displaying the first activity metric to display a second activity metric different from the first activity metric.

15. A method operable by a wearable electronic device comprising one or more sensors configured to generate sensor data, the wearable electronic device having stored thereon a watch check rule for causing a change to a display of the wearable electronic device, wherein the watch check rule includes data or logic that represents one or more patterns of movement indicative of a user of the wearable electronic device checking the display, the method comprising:

detecting, using the sensor data, that the user is performing a particular type of activity;
enabling the watch check rule based on the detection;
determining, based on sensor data generated by the one or more sensors during a first time period and while a first content is displayed on the display, that the user has made a bodily adjustment matching the one or more patterns of movement indicative of the user checking the display such that the watch check rule is satisfied;
in response to determining that the watch check rule is satisfied, causing a first change to the display, the first change causing the display displaying the first content to display a first activity metric different from the first content and indicative of the user's performance with respect to the particular type of activity;

logging first accelerometer data extracted from the sensor data generated during the first time period, the first accelerometer data comprising a first x-axis value and a first y-axis value;
extracting second accelerometer data from sensor data generated during a second time period, the second accelerometer data comprising a second x-axis value and a second y-axis value;
determining whether the second x-axis value of the second accelerometer data exceeds the first x-axis value of the logged first accelerometer data by a first threshold amount;
determining whether the second y-axis value of the second accelerometer data exceeds the first y-axis value of the logged first accelerometer data by a second threshold amount; and
in response to determining that (i) the second x-axis value exceeds the first x-axis value by the first threshold amount and (ii) the second y-axis value exceeds the first y-axis value by the second threshold amount, causing a second change to the display, the second change causing the display displaying the first activity metric to display the first content.

16. The method of claim 15, wherein causing the first change includes causing the display displaying a second activity metric different from the first activity metric to display the first activity metric.

17. The method of claim 15, further comprising:
obtaining sensor data generated by the one or more sensors during a third time period; and
calculating the first activity metric from the sensor data generated during the third time period.

18. The method of claim 17, wherein the first activity metric is at least one of a time, a pace, a speed, a distance, a mile split, a heart rate, a clock, a step count, a floor count, an estimation of calories burned, or an active minute count.

19. The method of claim 15, further comprising determining that the second x-axis value exceeds the first x-axis value by the first threshold amount when the second x-axis value exceeds the first x-axis value by the first threshold amount for a first threshold number of samples, and determining that the second y-axis value exceeds the first y-axis value by the second threshold amount when the second y-axis value exceeds the first y-axis value by the second threshold amount for a second threshold number of samples.

20. The method of claim 15, further comprising transforming each of one or more of the first and second x-axis values and the first and second y-axis values to an absolute value.

* * * * *